United States Patent
O'Brien

(10) Patent No.: US 10,499,894 B2
(45) Date of Patent: Dec. 10, 2019

(54) ORTHOPEDIC SURGICAL SYSTEM INCLUDING SURGICAL ACCESS SYSTEMS, DISTRACTION SYSTEMS, AND METHODS OF USING SAME

(71) Applicant: K2M, Inc., Leesburg, VA (US)

(72) Inventor: Keenan O'Brien, Broadlands, VA (US)

(73) Assignee: K2M, Inc., Leesburg, VA (US)

( * ) Notice: Subject to any disclaimer, the term of this patent is extended or adjusted under 35 U.S.C. 154(b) by 216 days.

(21) Appl. No.: 15/638,433

(22) Filed: Jun. 30, 2017

(65) Prior Publication Data

US 2017/0296160 A1 Oct. 19, 2017

Related U.S. Application Data

(63) Continuation-in-part of application No. 15/234,174, filed on Aug. 11, 2016, now Pat. No. 10,149,674.

(60) Provisional application No. 62/204,384, filed on Aug. 12, 2015, provisional application No. 62/204,386, filed on Aug. 12, 2015.

(51) Int. Cl.
| | |
|---|---|
| *A61B 17/02* | (2006.01) |
| *A61B 17/70* | (2006.01) |
| *A61B 17/15* | (2006.01) |
| *A61B 17/68* | (2006.01) |

(52) U.S. Cl.
CPC ........ *A61B 17/0206* (2013.01); *A61B 17/025* (2013.01); *A61B 17/0218* (2013.01); *A61B 17/151* (2013.01); *A61B 17/7077* (2013.01); *A61B 2017/0256* (2013.01); *A61B 2017/681* (2013.01)

(58) Field of Classification Search
CPC ........... A61B 1/32; A61B 17/02; A61B 90/50; A61B 17/0206
See application file for complete search history.

(56) References Cited

U.S. PATENT DOCUMENTS

| 196,600 A | 10/1877 | Shiland |
|---|---|---|
| 1,613,141 A | 1/1927 | Stein |
| 2,693,795 A | 11/1954 | Grieshaber |

(Continued)

FOREIGN PATENT DOCUMENTS

| WO | 2006017886 A1 | 2/2006 |
|---|---|---|
| WO | 2006119447 A1 | 11/2006 |
| WO | 2007038418 A2 | 4/2007 |

OTHER PUBLICATIONS

International Search Report from International Application No. PCT/US2011/055742 dated Feb. 3, 2012.

(Continued)

*Primary Examiner* — Andrew Yang
(74) *Attorney, Agent, or Firm* — Lerner, David, Littenberg, Krumholz & Mentlik, LLP

(57) ABSTRACT

A surgical access system includes a connector including an arm having first and second end portions, a coupling element having a body portion defining a cavity therein, and a gear assembly. The gear assembly includes a first gear disposed within the cavity of the coupling element and a second gear non-rotatably disposed at the first end portion of the arm. The first and second gears are meshingly engaged with each other such that rotation of the first gear results in rotation of the second gear which, in turn, causes the arm to pivot with respect to the coupling element.

18 Claims, 35 Drawing Sheets

(56) References Cited

U.S. PATENT DOCUMENTS

| | | |
|---|---|---|
| 2,701,562 A | 2/1955 | Sidney et al. |
| 3,129,706 A | 4/1964 | Reynolds |
| 3,192,928 A | 7/1965 | Horton |
| 3,227,156 A | 1/1966 | Gauthier |
| 3,724,449 A | 4/1973 | Gauthier |
| 3,749,088 A | 7/1973 | Kohlmann |
| 3,750,652 A | 8/1973 | Sherwin |
| 4,263,899 A | 4/1981 | Burgin |
| 4,300,541 A | 11/1981 | Burgin |
| 4,545,374 A | 10/1985 | Jacobson |
| 4,747,394 A | 5/1988 | Watanabe |
| 4,852,552 A | 8/1989 | Chaux |
| 4,924,857 A | 5/1990 | Mahmoodian |
| 4,926,849 A | 5/1990 | Downey |
| 4,966,130 A | 10/1990 | Montaldi |
| 4,989,587 A | 2/1991 | Farley |
| 5,167,223 A | 12/1992 | Koros et al. |
| 5,190,548 A | 3/1993 | Davis |
| 5,242,443 A | 9/1993 | Kambin |
| 5,339,801 A | 8/1994 | Poloyko et al. |
| 5,503,617 A | 4/1996 | Jako |
| 5,512,038 A | 4/1996 | O'Neal et al. |
| 5,520,608 A | 5/1996 | Cabrera et al. |
| 5,529,571 A | 6/1996 | Daniel |
| 5,582,577 A | 12/1996 | Lund et al. |
| 5,616,117 A | 4/1997 | Dinkier et al. |
| 5,667,520 A | 9/1997 | Bonutti |
| 5,697,944 A | 12/1997 | Lary |
| 5,707,359 A | 1/1998 | Bufalini |
| 5,707,362 A | 1/1998 | Yoon |
| 5,718,705 A | 2/1998 | Sammarco |
| 5,725,528 A | 3/1998 | Errico et al. |
| 5,728,046 A | 3/1998 | Mayer et al. |
| 5,769,783 A | 6/1998 | Fowler |
| 5,813,978 A | 9/1998 | Jako |
| 5,885,210 A | 3/1999 | Cox |
| 5,902,231 A | 5/1999 | Foley et al. |
| 5,902,233 A | 5/1999 | Farley et al. |
| 5,928,139 A | 7/1999 | Koros et al. |
| 5,931,777 A | 8/1999 | Sava |
| 5,944,658 A | 8/1999 | Koros et al. |
| 5,947,896 A | 9/1999 | Sherts et al. |
| 5,967,972 A | 10/1999 | Santilli et al. |
| 5,976,146 A | 11/1999 | Ogawa et al. |
| 6,099,547 A | 8/2000 | Gellman et al. |
| 6,139,493 A | 10/2000 | Koros et al. |
| 6,187,000 B1 | 2/2001 | Davison et al. |
| 6,200,322 B1 | 3/2001 | Branch et al. |
| 6,206,826 B1 | 3/2001 | Mathews et al. |
| 6,224,545 B1 | 5/2001 | Cocchia et al. |
| 6,241,659 B1 | 6/2001 | Bookwalter et al. |
| 6,270,501 B1 | 8/2001 | Freiberg et al. |
| 6,322,500 B1 | 11/2001 | Sikora et al. |
| 6,360,750 B1 | 3/2002 | Gerber et al. |
| 6,447,443 B1 | 9/2002 | Keogh et al. |
| 6,524,320 B2 | 2/2003 | DiPoto |
| 6,530,926 B1 | 3/2003 | Davison |
| 6,530,929 B1 | 3/2003 | Justis et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,553 B2 | 11/2003 | Davison et al. |
| 6,659,944 B2 | 12/2003 | Sharratt |
| 6,688,195 B1 | 2/2004 | Hsien |
| 6,743,206 B1 | 6/2004 | Smith et al. |
| 6,767,355 B2 | 7/2004 | Frova et al. |
| 6,796,422 B1 | 9/2004 | Lu |
| 6,800,084 B2 | 10/2004 | Davison et al. |
| 6,849,064 B2 | 2/2005 | Hamada |
| 6,869,398 B2 | 3/2005 | Obenchain et al. |
| 6,929,606 B2 | 8/2005 | Ritland |
| 6,945,933 B2 | 9/2005 | Branch et al. |
| 7,004,945 B2 | 2/2006 | Boyd et al. |
| 7,008,422 B2 | 3/2006 | Foley et al. |
| 7,011,660 B2 | 3/2006 | Sherman et al. |
| 7,056,321 B2 | 6/2006 | Pagliuca et al. |
| 7,056,329 B2 | 6/2006 | Kerr |
| 7,083,621 B2 | 8/2006 | Shaolian et al. |
| 7,108,705 B2 | 9/2006 | Davison et al. |
| 7,144,393 B2 | 12/2006 | DiPoto et al. |
| 7,150,714 B2 | 12/2006 | Myles |
| 7,160,300 B2 | 1/2007 | Jackson |
| 7,166,107 B2 | 1/2007 | Anderson |
| 7,179,261 B2 | 2/2007 | Sicvol et al. |
| 7,188,626 B2 | 3/2007 | Foley et al. |
| 7,250,052 B2 | 7/2007 | Landry et al. |
| 7,318,817 B2 | 1/2008 | Hamada |
| 7,494,463 B2 | 2/2009 | Nehls |
| 7,537,564 B2 | 5/2009 | Bonadio et al. |
| 7,588,575 B2 | 9/2009 | Colleran et al. |
| 7,615,079 B2 | 11/2009 | Flickinger et al. |
| 7,618,442 B2 | 11/2009 | Spitler et al. |
| 7,666,201 B2 | 2/2010 | Grayzel et al. |
| 7,758,584 B2 | 7/2010 | Bankoski et al. |
| 7,879,074 B2 | 2/2011 | Kwak et al. |
| 8,012,182 B2 | 9/2011 | Couedic et al. |
| 8,043,343 B2 | 10/2011 | Miller et al. |
| 8,097,027 B2 | 1/2012 | Lim et al. |
| 8,118,840 B2 | 2/2012 | Trieu et al. |
| 8,231,528 B1 | 7/2012 | Friedrich et al. |
| 8,251,901 B2 | 8/2012 | White et al. |
| 8,398,644 B2 | 3/2013 | Kirschman |
| 8,449,463 B2 | 5/2013 | Nunley et al. |
| 8,556,905 B2 | 10/2013 | Simonson |
| 8,979,749 B2 | 3/2015 | Gorek et al. |
| 9,131,934 B2 | 9/2015 | Strauss et al. |
| 9,848,863 B2 * | 12/2017 | Cryder ............... A61B 17/0206 |
| 2002/0077531 A1 | 6/2002 | Puchovsky et al. |
| 2002/0095139 A1 | 7/2002 | Keogh et al. |
| 2003/0004401 A1 | 1/2003 | Ball et al. |
| 2003/0149341 A1 | 8/2003 | Clifton |
| 2003/0171749 A1 | 9/2003 | Le Couedic et al. |
| 2003/0191371 A1 | 10/2003 | Smith et al. |
| 2003/0208203 A1 | 11/2003 | Lim et al. |
| 2004/0024291 A1 | 2/2004 | Zinkel |
| 2004/0068268 A1 | 4/2004 | Boyd et al. |
| 2004/0093000 A1 | 5/2004 | Kerr |
| 2004/0093001 A1 | 5/2004 | Hamada |
| 2004/0176665 A1 | 9/2004 | Branch et al. |
| 2004/0215199 A1 | 10/2004 | Zinkel |
| 2004/0230100 A1 | 11/2004 | Shluzas |
| 2004/0230191 A1 | 11/2004 | Frey et al. |
| 2005/0065517 A1 | 3/2005 | Chin |
| 2005/0070765 A1 | 3/2005 | Abdelgany et al. |
| 2005/0080320 A1 | 4/2005 | Lee et al. |
| 2005/0101985 A1 | 5/2005 | Hamada |
| 2005/0113644 A1 | 5/2005 | Obenchain et al. |
| 2005/0149035 A1 | 7/2005 | Pimenta et al. |
| 2005/0159650 A1 | 7/2005 | Raymond et al. |
| 2005/0159651 A1 | 7/2005 | Raymond et al. |
| 2005/0165408 A1 | 7/2005 | Puno et al. |
| 2005/0215866 A1 | 9/2005 | Kim |
| 2005/0216088 A1 | 9/2005 | McKinley et al. |
| 2005/0228376 A1 | 10/2005 | Boomer et al. |
| 2005/0234304 A1 | 10/2005 | Dewey et al. |
| 2005/0240209 A1 | 10/2005 | Hamada |
| 2005/0277812 A1 | 12/2005 | Myles |
| 2006/0052812 A1 | 3/2006 | Winer |
| 2006/0079894 A1 | 4/2006 | Colleran et al. |
| 2006/0084844 A1 | 4/2006 | Nehls |
| 2006/0142643 A1 | 6/2006 | Parker |
| 2006/0167487 A1 | 7/2006 | Hamada |
| 2006/0173454 A1 | 8/2006 | Spitler et al. |
| 2006/0178693 A1 | 8/2006 | Hamada |
| 2006/0195114 A1 | 8/2006 | Bertagnoli |
| 2006/0229614 A1 | 10/2006 | Foley et al. |
| 2006/0247645 A1 | 11/2006 | Wilcox et al. |
| 2006/0264962 A1 | 11/2006 | Chin et al. |
| 2006/0271057 A1 | 11/2006 | Shluzas et al. |
| 2006/0271096 A1 | 11/2006 | Hamada |
| 2006/0287730 A1 | 12/2006 | Segal et al. |
| 2007/0038216 A1 | 2/2007 | Hamada |
| 2007/0055247 A1 | 3/2007 | Jahng |
| 2007/0083267 A1 | 4/2007 | Miz et al. |

(56) References Cited

U.S. PATENT DOCUMENTS

| | | |
|---|---|---|
| 2007/0106123 A1 | 5/2007 | Gorek et al. |
| 2007/0129731 A1 | 6/2007 | Sicvol et al. |
| 2007/0156023 A1 | 7/2007 | Frasier et al. |
| 2007/0167954 A1 | 7/2007 | Sicvol et al. |
| 2007/0260125 A1 | 11/2007 | Strauss et al. |
| 2007/0270842 A1 | 11/2007 | Bankoski et al. |
| 2008/0021284 A1 | 1/2008 | Hestad et al. |
| 2008/0021285 A1 | 1/2008 | Drzyzga et al. |
| 2008/0027432 A1 | 1/2008 | Strauss et al. |
| 2008/0183046 A1 | 7/2008 | Boucher et al. |
| 2008/0255567 A1 | 10/2008 | Accordino |
| 2008/0262318 A1 | 10/2008 | Gorek et al. |
| 2008/0262501 A1 | 10/2008 | Chen et al. |
| 2009/0036746 A1 | 2/2009 | Blackwell et al. |
| 2009/0093684 A1 | 4/2009 | Schorer |
| 2009/0099605 A1 | 4/2009 | Fallin et al. |
| 2009/0131755 A1 | 5/2009 | White et al. |
| 2009/0187080 A1 | 7/2009 | Seex |
| 2009/0222044 A1 | 9/2009 | Gorek |
| 2009/0222046 A1 | 9/2009 | Gorek |
| 2009/0228110 A1 | 9/2009 | McClintock |
| 2010/0130827 A1 | 5/2010 | Pimenta et al. |
| 2010/0174146 A1 | 7/2010 | Miles et al. |
| 2011/0130634 A1 | 6/2011 | Solitario, Jr. et al. |
| 2012/0123432 A1 | 5/2012 | Kirschman |
| 2012/0190934 A1 | 7/2012 | Gorek et al. |
| 2012/0232350 A1 | 9/2012 | Seex |
| 2013/0158611 A1 | 6/2013 | Kirschman |
| 2013/0245383 A1 | 9/2013 | Friedrich et al. |
| 2013/0245384 A1 | 9/2013 | Friedrich et al. |

OTHER PUBLICATIONS

Japanese Unexamined Patent Application Publication No. 2007-512853.
Japanese Unexamined Patent Application Publication No. 2010-510841.
Japanese Office Action dated Aug. 4, 2015 in connection with corresponding Japanese Patent Application No. 2013-533013.
Australian Patent Examination Report dated Aug. 17, 2015 in connection with corresponding Australian Patent Application No. 2014203469.
About Endius/Corporate Overview. The Pioneer of Endoscopic Spine Fusion—Atavi System. (Internet Reference, 2002).
Aldrich, "Posterolateral microdiscectomy for cervical monoradiculopathy caused by posterolateral soft cervical disc dequestration", J. Neurosurg. 72:370-377 (1990).
Aronson, "The management of soft cervical disc protrusions using the Smith-Robinson approach", Clinical Neurosurgery 20:253-258 (1973).
Caspar, "A new surgical procedure for lumbar disc herniation causing less tissue damage through a microsurgical approach", Adv Neurosurg 4:72-80 (1977).
Cloward, "The Anterior Approach for Removal of Ruptured Cervical Disks", Presented at the meeting of the Harvey Cushing Society, Washington, DC, Apr. 22, 1958, pp. 602-617.
Fessler, et al., "Minimally Invasive Cervical Microendoscopic Foraminotomy: An Initial Clinical Experience", Neurosurgery 51(2):2-10 (2002).
Fessler, et al., "A minimally invasive technique for decompression of the lumbar spine", Spine 27:432-438 (2002).
Foley, et al., "Microendoscopic Discectomy", Techniques in Neurosurgery 3(4):301-307 (1997).
Henderson, et al., "Posterior-Lateral Foraminotomy as an Exclusive Operative Technique for Cervical Radiculopathy: A Review of 846 consecutively Operated Cases", Neurosurgery, 13(5): 504-521 (1983).
Hermantin, et al., "A Prospective, Randomized Study Comparing the Results of Open discectomy with Those of Video-Assisted Arthroscopic Microdiscectomy", The Journal of Bone and Joint Surgery 81A(7):958-965 (1999).
Kawaguchi, et al., "Back Muscle Injury After Posterior Lumbar Spine Surgery", Spine, 21(8):941-944 (1996).
Lin, et al., "Posterior Lumbar Interbody Fusion", Clinical Orthopedics and Related Research, No. 180, pp. 154-168 (1983).
Lin, "Posterior Lumbar Interbody Fusion Technique: Complications and Pitfalls", PLIF Complications and Pitfalls, No. 193, pp. 90-102 (1985).
Malis, "Instrumentation and Techniques in Microsurgery", Clinical Neurosurgery, 26:626-636 (1979).
Rantanen, et al., "The Lumbar Multifidus Muscle Five Years After Surgery for a Lumbar Intervertebral Disc Herniation", Spine, 18(5):268-274 (1993).
Roh, et al., "Endoscopic Foraminotomy Using MED System in Cadaveric Specimens", Spine, 25(2):260-264 (2000).
Sihvonen, et al., "Local denervation atrophy of paraspinal muscles in postoperative failed back syndrome", Spine 18:575-581 (1993).
Styf, et al., "The Effects of External Compression by Three Different Retractors on Pressure in the Erector Spine Muscles During and After Posterior Lumbar Spine Surgery in Humans", Spine, 23(3):354-358 (1998).
Tsai, et al., "Microscopic Laminotomies for Degenerative Lumbar Spinal Stenosis", Journal of Spinal disorders, 11 (5):389-394 (1998).
Weber et al, "Posterior surgical approach to the lumbar spine and its effect on the multifidus muscle", Spine 22:1765-1772 (1992).
Weiner, et al., "Microdecompression for Lumbar Spinal Canal Stenosis", Spine, 24(21):2268-2272 (1999).
Supplementary Partial European Search Report from Application No. EP 08746083.8 dated Dec. 3, 2014.

* cited by examiner

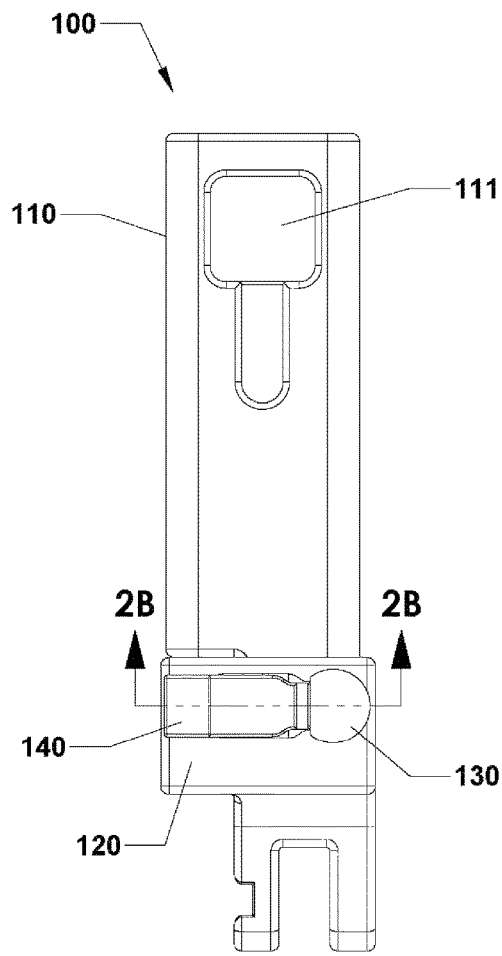
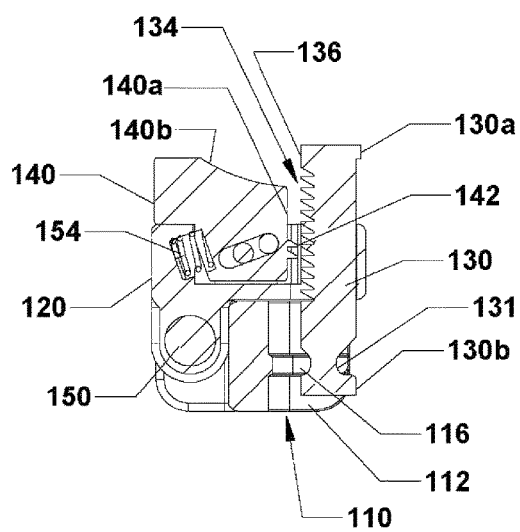
FIG. 2A
FIG. 2B

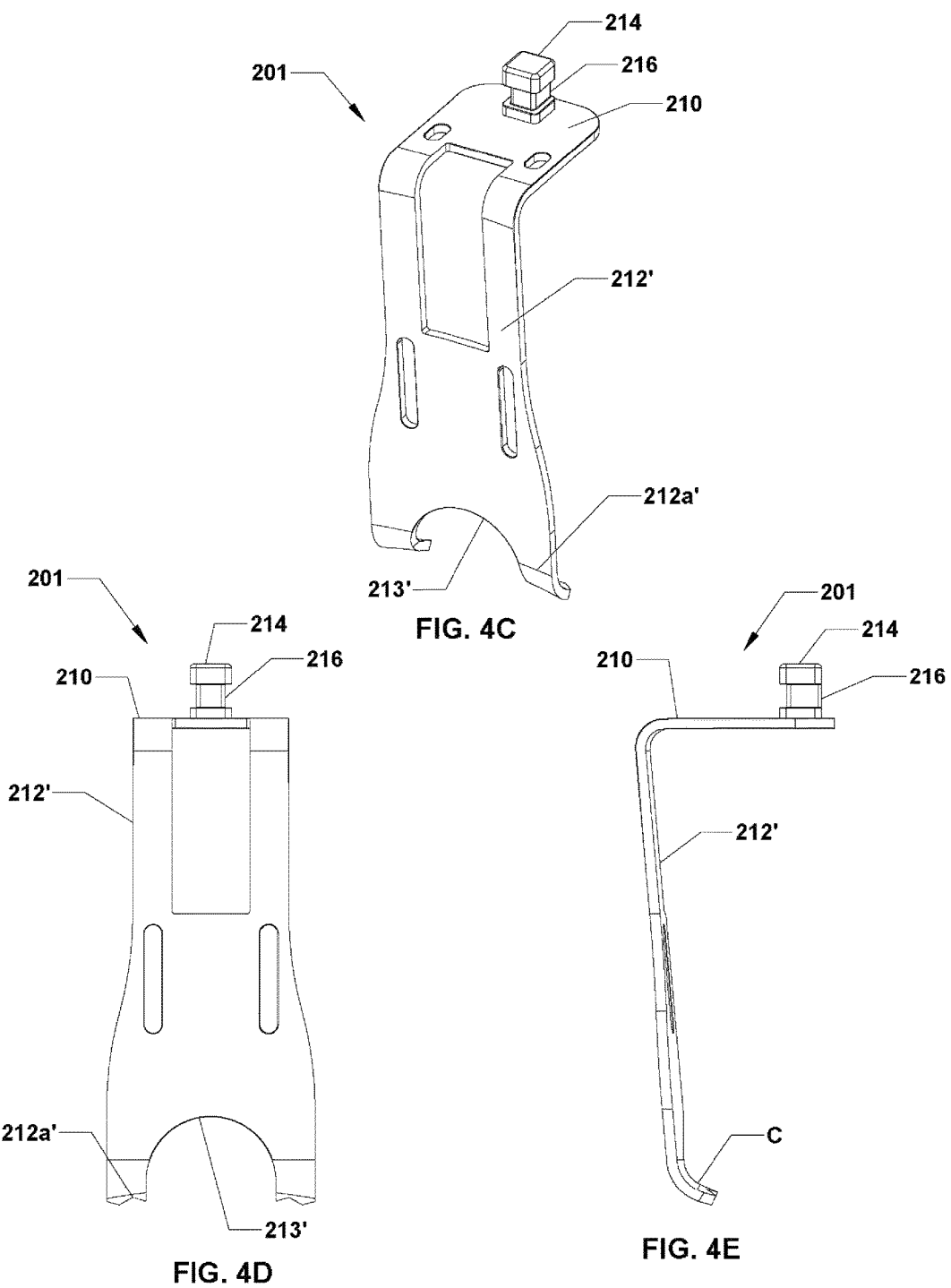

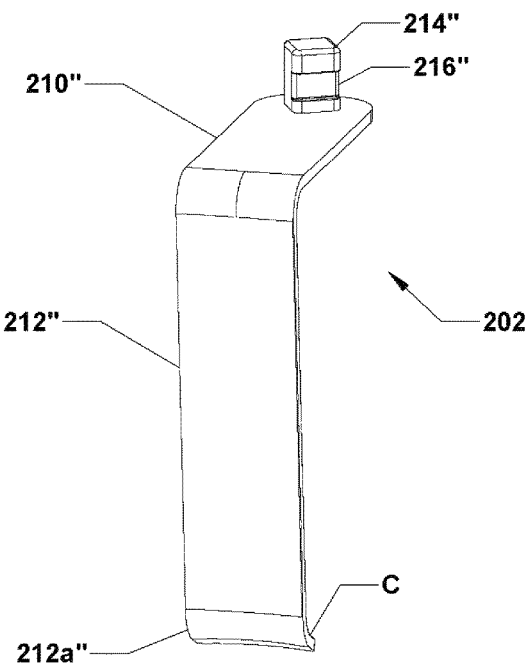
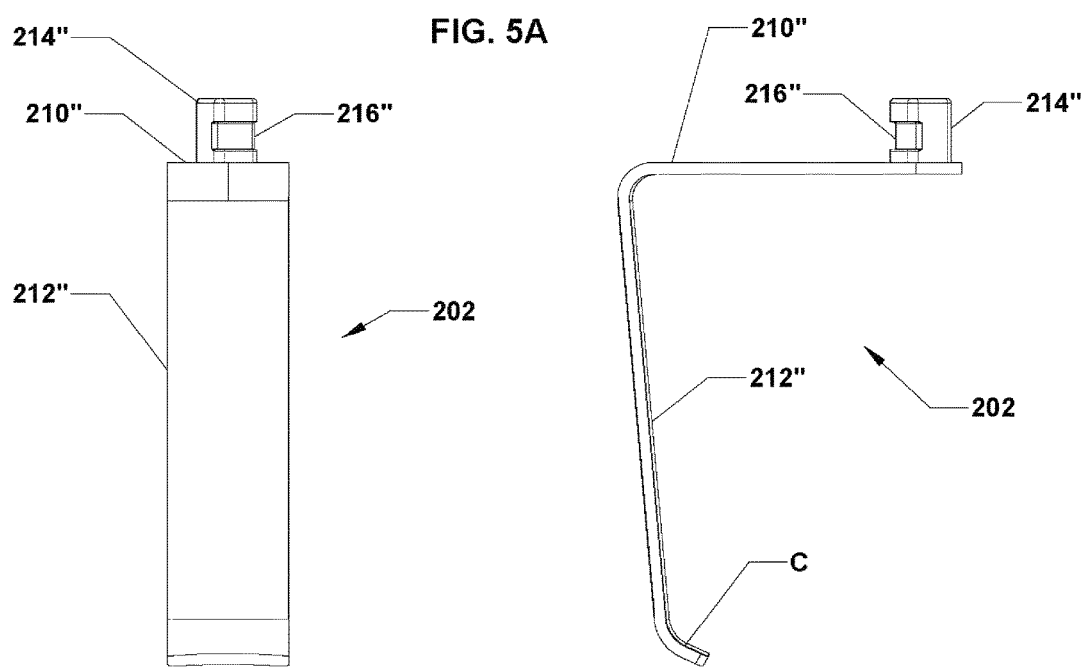
FIG. 5A
FIG. 5B
FIG. 5C

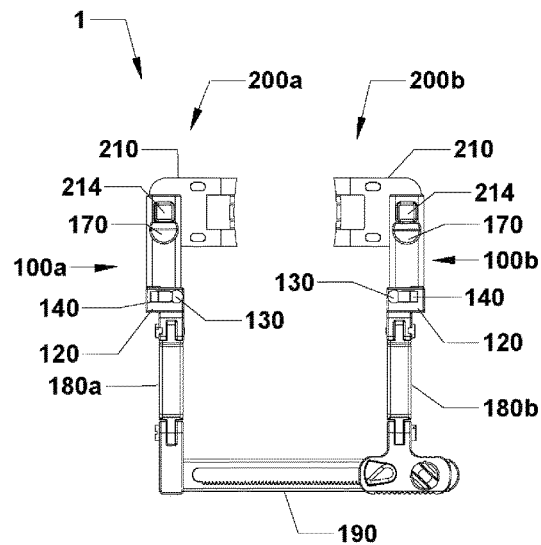
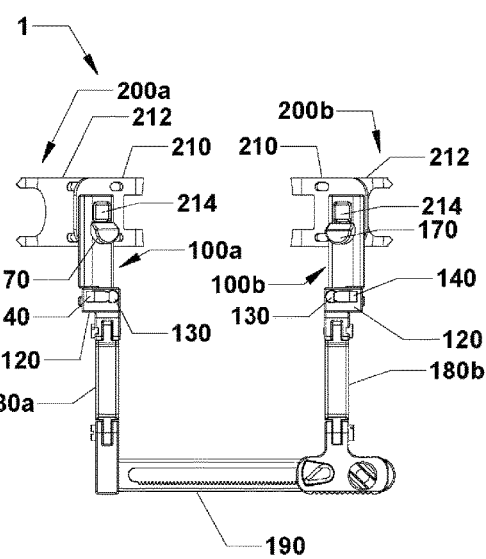
FIG. 8A
FIG. 9A
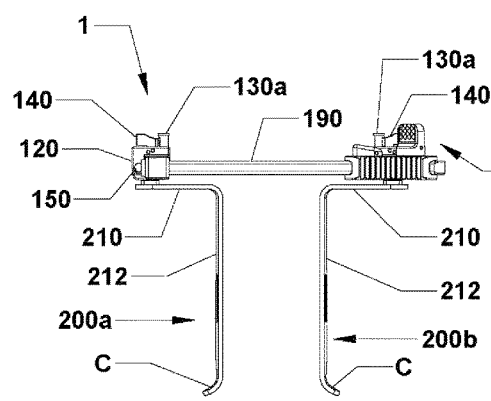
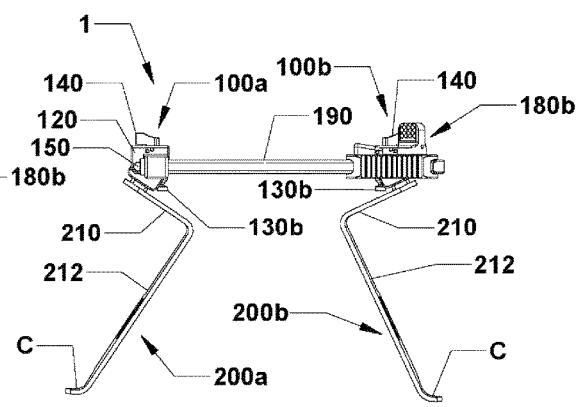
FIG. 8B
FIG. 9B

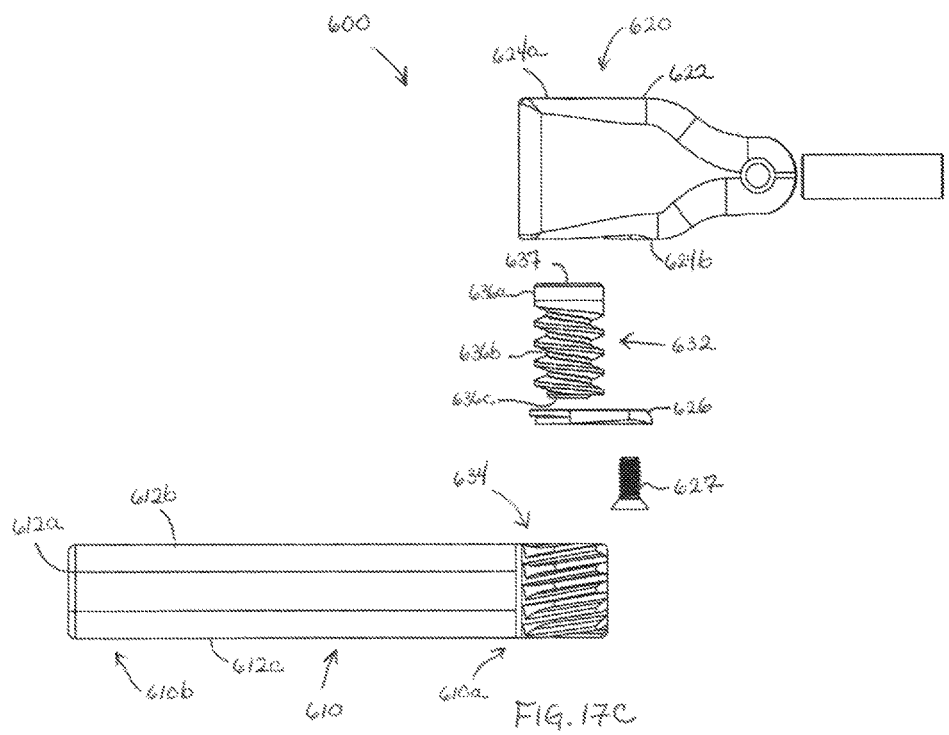
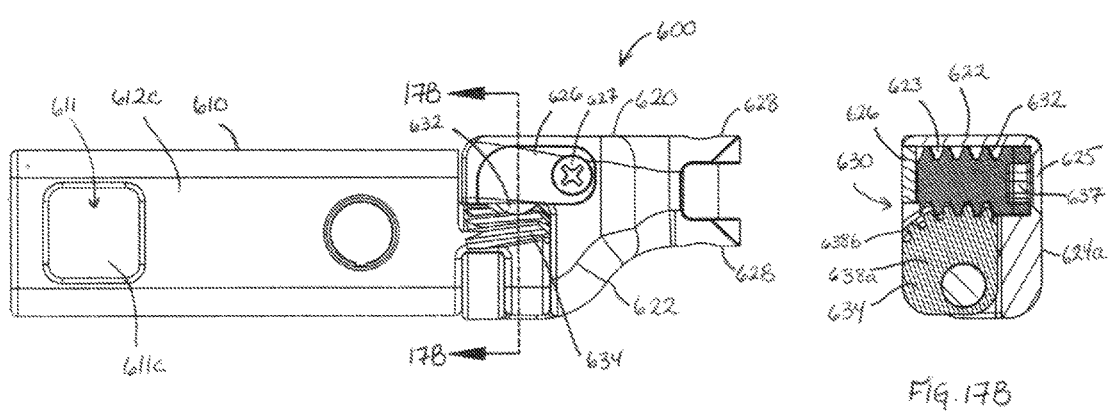
FIG. 17C
FIG. 17A  FIG. 17B

ORTHOPEDIC SURGICAL SYSTEM INCLUDING SURGICAL ACCESS SYSTEMS, DISTRACTION SYSTEMS, AND METHODS OF USING SAME

CROSS-REFERENCE TO RELATED APPLICATIONS

This application is a continuation-in-part of U.S. patent application Ser. No. 15/234,174, filed on Aug. 11, 2016, which claims the benefit of, and priority to, U.S. Provisional Patent Application Ser. No. 62/204,384, filed on Aug. 12, 2015, and U.S. Provisional Patent Application Ser. No. 62/204,386, filed on Aug. 12, 2015, the entire contents of each of which are hereby incorporated herein by reference.

TECHNICAL FIELD

The present disclosure relates generally to orthopedic surgical systems, and more particularly, to surgical access systems for separating tissue in a surgical field to increase visualization of the surgical field and surgical distraction systems for separating adjacent vertebral bodies, and methods of using the same.

BACKGROUND

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disease, the effects of aging, or physical trauma resulting in damage to the spine has been treated in many instances by fixation or stabilization of the effected vertebra. A wide variety of spinal fixation apparatuses have been employed in surgical procedures for correcting spinal injuries and the effects of spinal diseases.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the intervertebral discs. Corpectomy involves removal of the vertebral body as well as the adjacent intervertebral discs.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (bone knitting) solves the problem of instability.

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. As is typical, the intervertebral spaces are accessed either anteriorly or posteriorly. It would be desirable to access the intervertebral spaces via an approach that provides greater access to the surgical area while applying the least amount of stress to the surrounding tissue.

Additionally, one of the challenges during surgery is to ensure that the vertebral bodies can maintain parallel distraction so as not to move the spine out of alignment.

Therefore, a need exists for systems and/or devices used in spinal surgery that provides greater access and visualization of a surgical area while applying the least amount of stress to the surrounding tissue and/or maintains alignment and spacing of the vertebral bodies and rigid attachment to the vertebral bodies.

SUMMARY

In accordance with an aspect of the present disclosure, a surgical access system includes a beam, a first support operably coupled to the beam, and a first connector operably connected to the first support. The first connector includes an arm including a first end portion and a second end portion, a coupling element including a body portion defining a cavity therein, and a gear assembly. The gear assembly includes a first gear disposed within the cavity of the coupling element and a second gear non-rotatably disposed at the first end portion of the arm. The first and second gears are meshingly engaged with each other such that rotation of the first gear results in rotation of the second gear which, in turn, causes the arm to pivot with respect to the coupling element.

In embodiments, the first gear includes a head portion and an elongated threaded body portion terminating at a distal end. An opening of the first cavity may be defined in a front surface of the coupling element, and the head portion of the first gear may be accessible through the opening for rotating the first gear. In some embodiments, the first gear is a worm screw.

In embodiments, the second gear includes a rounded body portion having a toothed outer surface. In some embodiments, the second gear is a worm wheel.

The second end portion of the arm may include a cavity having a receiving element disposed therein. The receiving element may include an engaging portion movable between a locked state and an unlocked state. In some embodiments, the surgical access system further includes a first retractor blade having a planar portion including a protruding portion having a grooved defined therein, and a blade portion extending along a different plane than the planar portion. The protruding portion is releasably engaged with the engaging portion of the receiving element.

In embodiments, the surgical access device further includes a second support operably coupled to the beam, a second connector operably connected to the second support, and a second retractor blade releasably engaged to the second connector.

In accordance with another aspect of the present disclosure, a surgical access system includes a first support, a second support, a cross bar interconnecting the first and second supports, and a first connector operably connected to the cross bar. The first connector includes an arm including a first end portion and a second end portion, a coupling element including a body portion defining a cavity therein, and a gear assembly. The gear assembly includes a first gear disposed within the cavity of the coupling element and a second gear non-rotatably disposed at the first end portion of the arm. The first and second gears are meshingly engaged with each other such that rotation of the first gear results in rotation of the second gear which, in turn, causes the arm to pivot with respect to the coupling element.

In embodiments, the first gear includes a head portion, an elongated threaded body portion, and a tail portion. A first opening of the cavity may be defined in a front surface of the coupling element, and the head portion of the first gear may be accessible through the first opening for rotating the first gear. In some embodiments, the first gear is a worm screw.

In embodiments, the second gear includes a rounded body portion having a toothed outer surface. In some embodiments, the second gear is a worm wheel. The second gear may be integrally formed on the first end portion of the arm.

The second end portion of the arm may include a cavity having a receiving element disposed therein. The receiving element may include an engaging portion movable between a locked state and an unlocked state. In some embodiments, the surgical access system further includes a first retractor blade having a planar portion including a protruding portion having a grooved defined therein, and a blade portion extending along a different plane than the planar portion. The protruding portion is releasably engaged with the engaging portion of the receiving element.

In embodiments, the surgical access device includes a second connector operably connected to the cross bar.

In accordance with an aspect of the present disclosure, a surgical access system includes a first connector including an arm, a coupling element, a rod, and a ridged slider. The arm includes first and second notched sections disposed in opposed lateral sides of the arm. The coupling element includes a body section defining an opening therethrough, and opposed tabs protruding from the body section that are configured to receive the second notched section of the arm therebetween such that the arm is pivotably coupled to the coupling element. The rod includes a shaft having a plurality of angled grooves defined partially along a length thereof. The rod extends through the opening of the coupling element and the first notched section of the arm. The ridged slider includes a first surface having a plurality of ridges extending along a partial length thereof. The ridged slider extends through the coupling element with the plurality of ridges operably engaged with the plurality of angled grooves of the rod.

The first notched section of the arm of the first connector may include a connecting element and the rod may include a circumferential groove engaged with the connecting element.

In embodiments, the first connector has a closed position in which the arm is adjacent to the coupling element, and an open position in which the arm is angled with respect to the coupling element.

The arm of the first connector may include a cavity having a receiving element disposed therein. The receiving element may include an engaging portion movable between a locked state and an unlocked state.

In embodiments, the surgical access system further includes a first retractor blade having a planar portion including a protruding portion having a grooved defined therein, and a blade portion. The planar and blade portions extend along different planes. In some embodiments, the protruding portion of the first retractor blade is releasably engaged with the engaging portion of the receiving element.

The surgical access device may further include a second connector and a second retractor blade. The surgical access device may further include first and second supports, and a beam. The first retractor blade may be coupled to the first support and the second retractor blade may be coupled to the second support. The first support may be fixed to the beam and the second support may be slidably mounted on the beam.

In embodiments, the surgical access device further includes an extension device having a first extension arm pivotably coupled to a second extension arm. The second extension arm includes a protruding portion having a groove defined therein. In some embodiments, the protruding portion of the extension device is releasably engaged with the engaging portion of the receiving element. In certain embodiments, the extension device includes a channel releasably engaged with the protruding portion of the first retractor blade.

In accordance with another aspect of the present disclosure, a surgical distraction system includes a distractor device including first and second elongated members pivotably coupled together. Each of the first and second elongated members includes a flat portion disposed on a lateral side thereof. The flat portions are substantially parallel to each other and in abutting relationship when the distractor device is in a closed position, and the flat portions are substantially parallel to each other and laterally spaced apart when in an open position.

In embodiments, each of the first and second elongated members of the distractor device includes a partial lumen extending partially along a length thereof substantially perpendicularly from the flat portion.

The surgical distraction system may further include a plurality of pins releasably engaged with the partial lumens of the first and second elongated members of the distractor device. Each pin of the plurality of pins may include at least one protrusion and the partial lumens may include at least one detent configured to receive the at least one protrusion.

In embodiments, the distractor device includes a handle including a biasing mechanism configured to bias the distractor device in the closed position.

In accordance with an aspect of the present disclosure, a method of creating separation between adjacent vertebral bodies includes inserting first and second pins into adjacent vertebral bodies, securing first and second elongated members of a distractor device to the first and second pins, the first and second elongated members pivotably coupled together, and each of the first and second elongated members including a flat portion disposed on a lateral side thereof, the flat portions being substantially parallel to each other and in an abutting relationship when the distractor device is in a closed position, and the flat portions being substantially parallel to each other and laterally spaced apart when the distractor device is in an open position, and manipulating a handle of the distractor device to move the distractor device to the open position to apply a distraction force to the adjacent vertebral bodies.

In embodiments, securing the first and second elongated members of the distractor device to the first and second pins includes positioning the distractor device between the first and second pins, and manipulating the handle of the distractor device to move the first and second elongated members of the distractor device into contact with the first and second pins to releasably secure the first and second elongated members to the first and second pins.

The method may further include inserting first and second retractor blades of a surgical access system into an opening in a patient, and moving at least one of the first and second retractor blades to increase a size of the opening.

In embodiments, the method further includes manipulating the handle of the distractor device to move the distractor device to the closed position to remove the distraction force, and removing the distractor device and the first and second pins from the adjacent vertebral bodies.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 2A is a front view of the connector of FIG. 1A in a straight or closed position;

FIG. 2B is a cross-sectional view of the connector of FIG. 2A, taken along line 2B-2B of FIG. 2A;

FIG. 4C is a perspective view of a tapered retractor blade in accordance with another embodiment of the present disclosure;

FIG. 4D is a front view of the tapered retractor blade of FIG. 4C;

FIG. 4E is a side view of the tapered retractor blade of FIGS. 4C and 4D;

FIG. 5A is a perspective view of an angled retractor blade in accordance with yet another embodiment of the present disclosure;

FIG. 5B is a front view of the angled retractor blade of FIG. 5A;

FIG. 5C is a side view of the angled retractor blade of FIGS. 5A and 5B;

FIG. 8A is a top view of the surgical access system of FIG. 7A, with retractor blades coupled thereto;

FIG. 8B is a side view of the surgical access system of FIG. 8A;

FIG. 9A is a top view of the surgical access system of FIG. 8A, with retractor blades coupled thereto and in an angled position;

FIG. 9B is a side view of the surgical access system of FIGS. 7B and 9A;

FIG. 17A is a back view of a connector in accordance with another embodiment of the present disclosure;

FIG. 17B is a cross-sectional view of the connector of FIG. 17A, taken along line 17B-17B of FIG. 17A;

FIG. 17C is a side view of the connector of FIG. 17A, with parts separated;

DETAILED DESCRIPTION

Figure 1A:
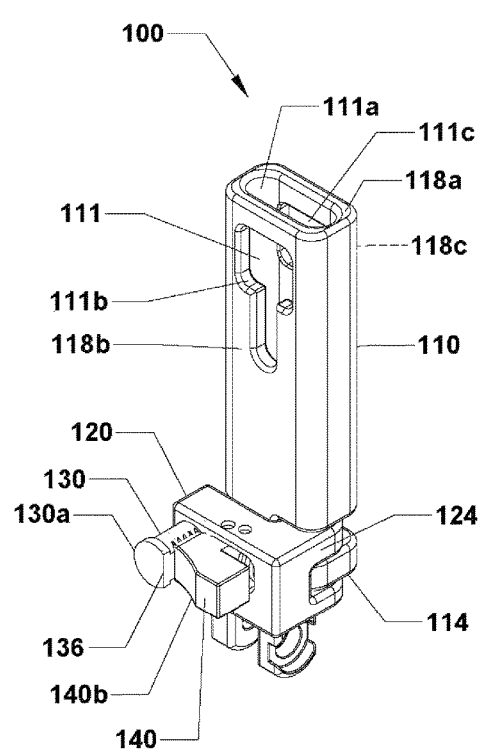
FIG. 1A is a perspective view of a connector in accordance with an embodiment of the present disclosure.

Embodiments of the present disclosure are now described in detail with reference to the drawings in which like reference numerals designate identical or corresponding elements in each of the several views. Throughout this description, the term "proximal" refers to a portion of a system, device, or component thereof that is closer to a clinician, and the term "distal" refers to the portion of the system, device, or component thereof that is farther from the clinician.

Figure 1B:
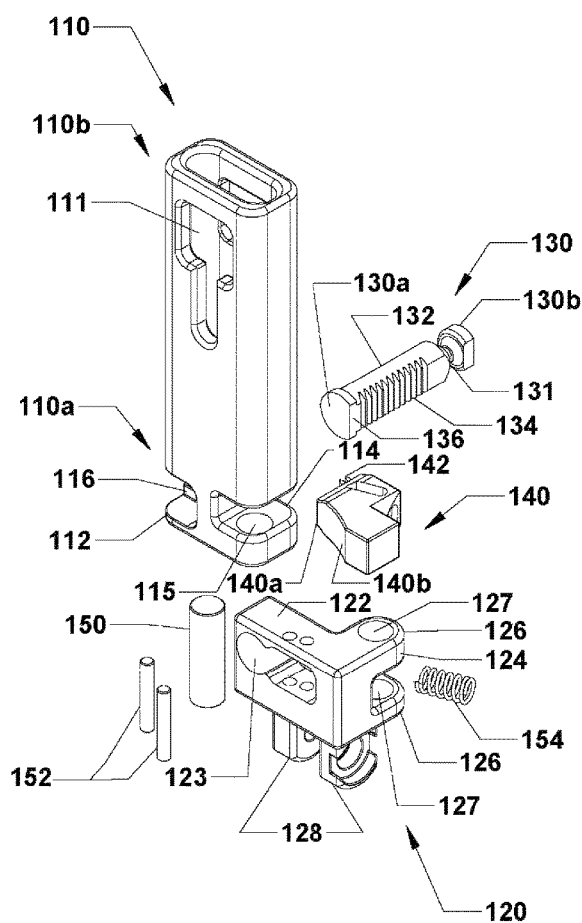
FIG. 1B is an exploded view of the connector of FIG. 1A.

Referring now to the drawings, FIGS. 1A and 1B illustrate a connector 100 configured and adapted for a minimally invasive surgical procedure to access, for example, the thoracic or lumbar vertebrae, in accordance with an embodiment of the present disclosure. The connector 100 is suitable for use with a retractor or surgical access system 2 (see FIG. 11) as will be described in detail hereinbelow. The connector 100 includes an arm 110, a coupling element 120, a rod 130, and a ridged slider 140. The arm 110 is configured and dimensioned to receive and support the coupling element 120 which, in turn, is configured and dimensioned to receive and support the rod 130 and the ridged slider 140.

The arm 110 extends along a longitudinal axis "X" (FIG. 6C), and includes a first end portion 110a and a second end portion 110b. The first end portion 110a includes a first notched section 112 disposed in a lateral side of the arm 110 that is configured and dimensioned to receive the rod 130, and a second notched section 114 disposed in an opposed lateral side of the arm 110 that is configured to receive a tab 126 of the coupling element 120. The first notched section 112 includes a connecting element 116 that is configured and dimensioned to engage a circumferential groove 131 of the rod 130. In embodiments, the connecting element 116 is a ridge or raised surface that extends from and wraps around an interior wall of the first notched section 112 (see e.g., FIG. 6B), and in some embodiments, the connecting element is substantially "U" or "C" shaped. It is contemplated that other shapes, textures, and/or configurations of the connecting element are possible so long as the connecting element 116 can releasably engage the circumferential groove 131 of the rod 130. The second notched section 114 includes a pair of opposed openings 115 configured to receiving a fixation pin 150 for securing the coupling element 120 to the arm 110. The arm 110 is rotatable about the fixation pin 150.

The second end portion 110b of the arm 110 includes a cavity 111 defined therein that is configured and dimensioned to house a receiving element 160 (see e.g., FIG. 6B), as described in further detail below. The cavity 111 is open at a first opening 111a defined in a proximal surface 118a of the arm 110, a second opening 111b defined in a front surface 118b of the arm 110, and a third opening 111c defined in a back surface 118c of the arm 110.

The coupling element 120 includes a body section 122 and a protruding section 124 integrally formed with and extending from a side surface of the body section 122. The body section 122 includes an opening 123 extending transverse through the body 122 that is configured and dimensioned to receive the rod 130 and the ridged slider 140. The protruding section 124 includes a pair of opposed tabs 126 configured to receive the second notched section 114 of the arm 110 therebetween. Each tab of the pair of opposed tabs 126 includes an opening 127 defined therethrough that is configured to receive the fixation pin 150 for securing the coupling element 120 to the arm 110, as described above. Retaining features 128 extend from a distal surface of the body section 122 of the coupling element 120 for coupling with a support 180 (see e.g., FIG. 7A).

The rod 130 includes a shaft 132 that extends between a first end 130a and a second end 130b of the rod 130. While the rod 130 is shown as substantially circular and having a circumference, it should be understood that the rod may be any shape, such as substantially square or angled. The shaft 132 includes a plurality of angled grooves 134 defined partially along a length of one side of the shaft 132. It should be understood, however, that the plurality of angled grooves 134 may extend around the circumference of the shaft 132.

The plurality of angled grooves 134 are disposed at an angle with respect to the shaft 132 and, in embodiments, the plurality of angled grooves 134 are disposed within a range of about 30° to about 40°. It should be understood that the plurality of angled grooves 134 may be disposed at any angle so long as they are configured to engage a plurality of ridges 142 disposed on the ridged slider 140, as described in further detail below. Additionally or alternatively, the shaft 132 of the rod 130 may include any textured pattern partially along its length and/or around its circumference so long as the textured pattern is configured to engage the ridged slider 140 (i.e., the shaft and the ridged slider have complementary configurations).

The first end 130a of the rod 130 includes a flattened side 136 located on the same side of the rod 130 as the plurality of angled grooves 134. The first end 130a of the rod 130 has a circumference that is greater than the circumference of the shaft 132. The larger circumference of the first end 130a aids in preventing the rod 130 from moving completely through the first opening 123 of the coupling element 120.

A circumferential groove 131 is defined between the second end 130b of the rod 130 and the shaft 132 in longitudinally spaced relation relative to the plurality of angled grooves 134. It should be understood that the circumferential groove 131 may be any shape or form so long as it is configured to engage the connecting element 116 in the first notched section 112 of the arm 110, as discussed above.

The ridged slider 140 includes a first surface 140a having a plurality of ridges 142 extending along a partial length thereof. The plurality of ridges 142 is disposed at an angle with respect to the first surface 140a to engage the plurality of angled grooves 134 of the rod 130, as discussed above. The plurality of ridges 142 may be any shape or form so long as they are configured to engage the plurality of angled grooves 134 of the rod 130. In embodiments, the ridged slider 140 acts as a pawl with the plurality of angled grooves 134 of the rod 130.

The ridged slider 140 includes a beveled surface 140b. The angle of the beveled surface 140b may be shallow (e.g., no bevel) or deep (e.g., almost 90°), or any angle therebetween. The angle of the beveled surface 140b affects the ability to apply a force to the ridged slider 140 by a user.

The ridged slider 140 is connected to the coupling element 120 with at least one connection pin 152 such that the first surface 140a of the ridged slider 140 is adjacent to the rod 130. The ridged slider 140 is operably coupled to a biasing member 154, such as a spring, disposed between the ridged slider 140 and an inner surface of the coupling element 120 to bias the ridged slider 140 towards engagement with the rod 130 thereby defining a locked state.

Referring now to FIGS. 2A and 2B, the connector 100 is shown in a straight or closed position. The arm 110 is coupled to the coupling element 120 via fixation pin 150. The rod 130 extends through the opening 123 (FIG. 1B) in the coupling element 120 and the circumferential groove 131 of the rod 130 is engaged with the connecting element 116 of the first notched section 112 of the arm 110. The ridged slider 140 also extends through the opening 123 of the coupling element 120 and is operatively engaged with the biasing member 154 so that the ridged slider 140 is biased towards the locked state. In the locked state, the plurality of ridges 142 on the first surface 140a of the ridged slider 140 is engaged with the plurality of angled grooves 134 of the rod 130.

Figures 3A, 3B:
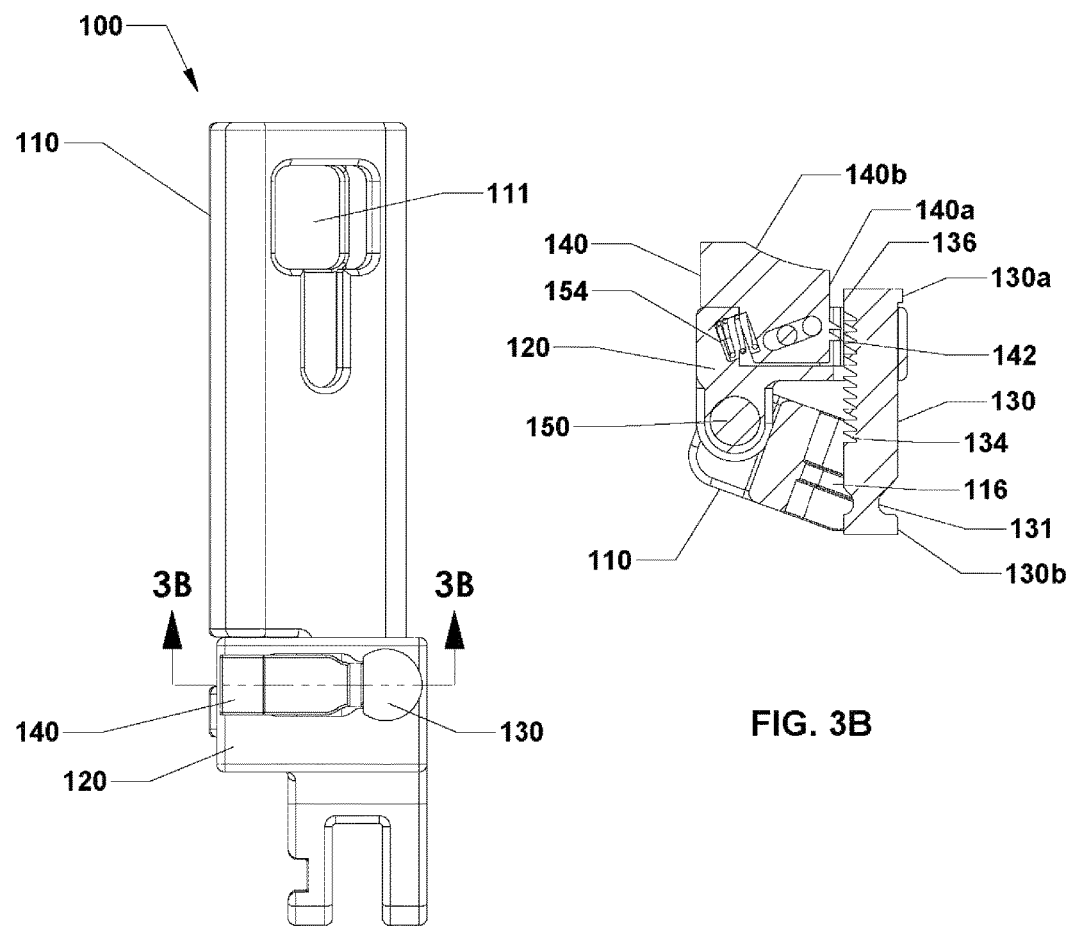
FIG. 3A is a front view of the connector of FIG. 1A in an angled or open position.
FIG. 3B is a cross-sectional view of the connector of FIG. 3A, taken along line 3B-3B of FIG. 3A.

The arm 110 of the connector 100 can move from the straight or closed position (FIGS. 2A and 2B) to an angled or open position, as shown in FIGS. 3A and 3B. A user applies a force to the first end 130a of the rod 130 thereby causing the plurality of angled grooves 134 to disengage from the plurality of ridges 142 of the ridged slider 140. Because the circumferential groove 131 of the rod 130 is engaged with the connecting element 116 of the arm 110, the arm 110 rotates about the fixation pin 150 to the angled or open position. Once the force is removed, the plurality of ridges 142 of the ridged slider 140 engages the plurality of angled grooves 134 of the rod 130 along a portion closer to the first end 130a of the rod 130 thereby retaining the connector 100 in the angled or open position. It should be noted that the rod 130 can continue to move upon an application of a force thereto so long as the plurality of ridges 142 of the ridged slider 140 is engaged with the plurality of angled grooves 134 of the rod 130. It should be understood that the rod 130 may only move in one direction due to the angle of the plurality of grooves 134 when the plurality of ridges 142 of the ridged slider 140 are engaged with the plurality of angled grooves 134. As discussed below, the rod 130 may be moved in two directions when the ridged slider 140 is in an unlocked state and the plurality of ridges 142 are disengaged from the plurality of angled grooves 134.

The arm 110 may also move from an angled or open position to a straight or closed position, e.g., from the angled or open position of FIGS. 3A and 3B to the straight or closed position of FIGS. 2A and 2B. A user applies a force to the beveled surface 140b of the ridged slider 140 which, in turn, causes the ridged slider 140 to engage the biasing member 154 thereby moving the ridged slider 140 from a locked state to an unlocked state, and away from the rod 130. In the unlocked state, the ridged slider 140 actively engages the biasing member 154 and the plurality of ridges 142 of the ridged slider 140 disengages from the plurality of angled grooves 134 of the rod 130. The arm 110 can then be rotated around the fixation pin 150 to the straight or closed position. Once the force is removed from the beveled surface 140b of the ridged slider 140, the biasing member 154 is disengaged and the ridged slider 140 returns to the locked state. Specifically, the ridged slider 140 slides back towards the rod 130 so that the plurality of ridges 142 engage the plurality of angled grooves 134 to retain the arm 110 in the straight or closed position.

Figure 10A:
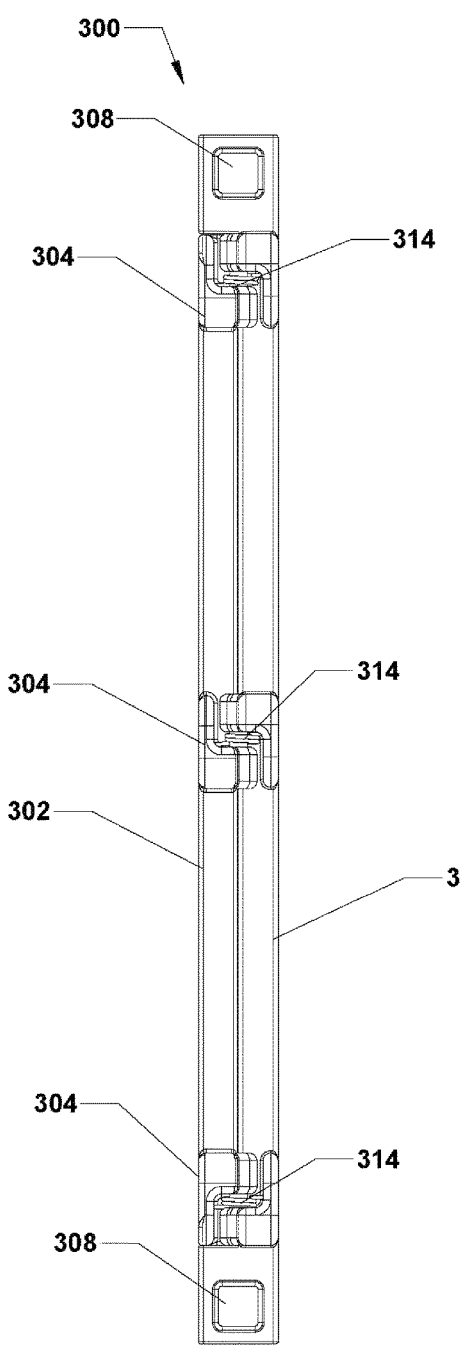
FIG. 10A is a top view of an extension device in accordance with an embodiment of the present disclosure.
Figure 10B:
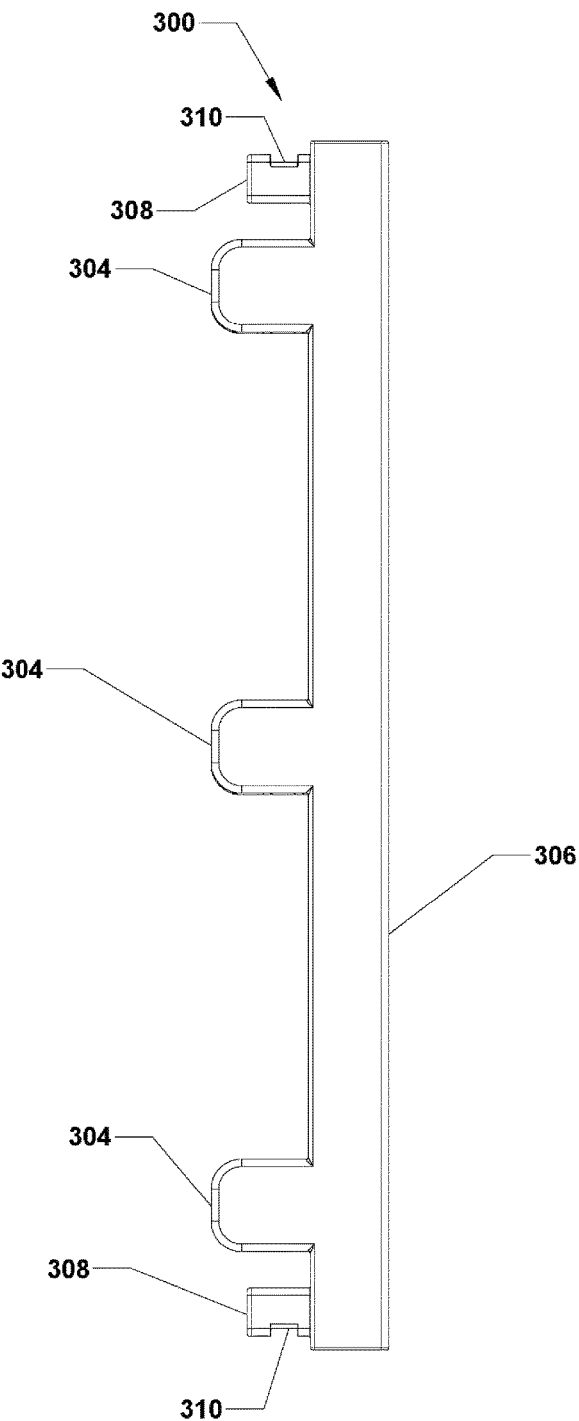
FIG. 10B is a side view of the extension device of FIG. 10A.
Figure 10C:
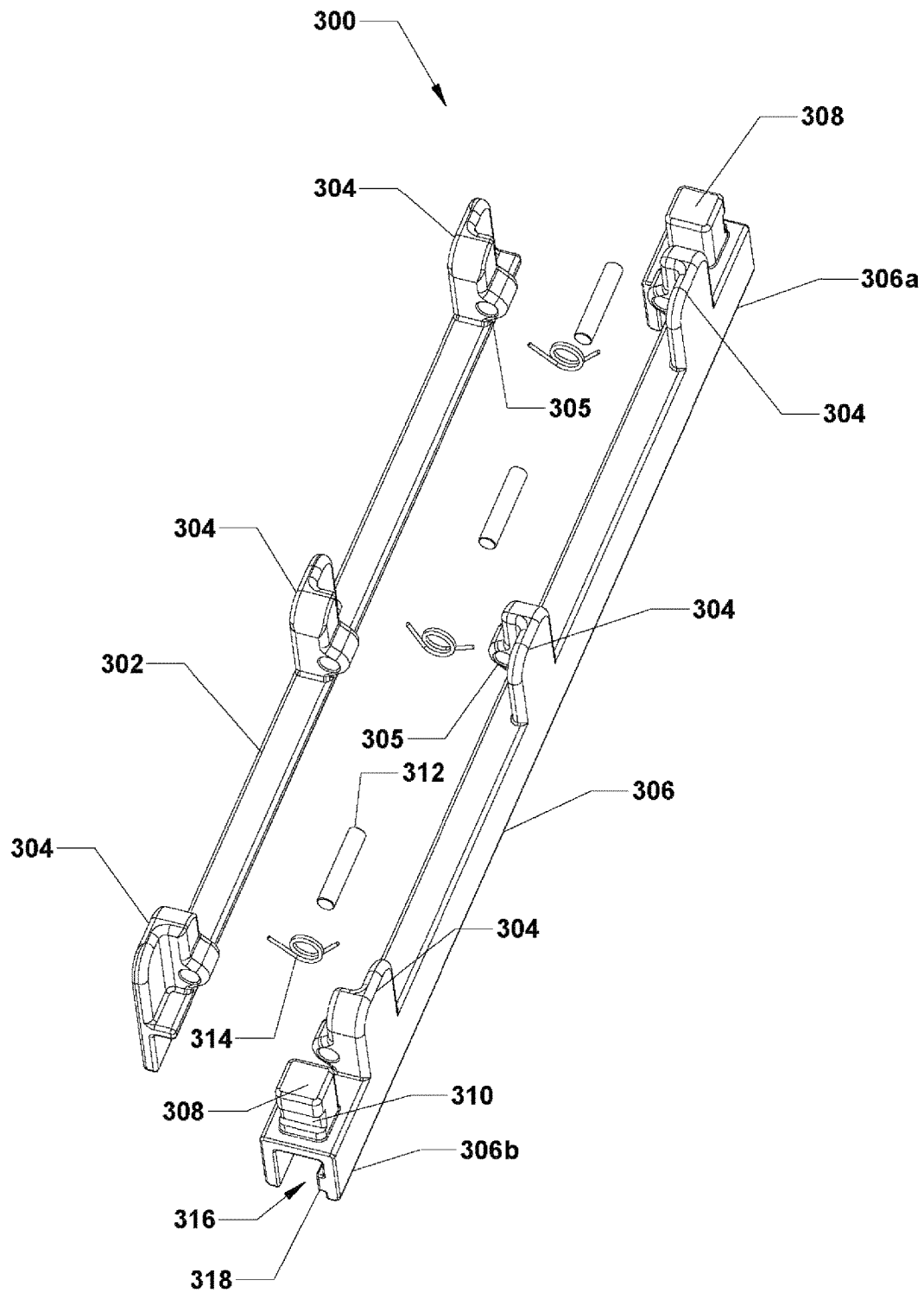
FIG. 10C is an exploded view of the extension device of FIGS. 10A and 10B.

The cavity 111 of the arm 110 is configured and dimensioned to releasably secure a protruding portion of a retractor blade or a protruding portion of an extension device thereto. Exemplary retractor blades are shown in FIGS. 4A-5E, and an exemplary extension device is shown in FIGS. 10A-10C.

Figures 4A, 4B:
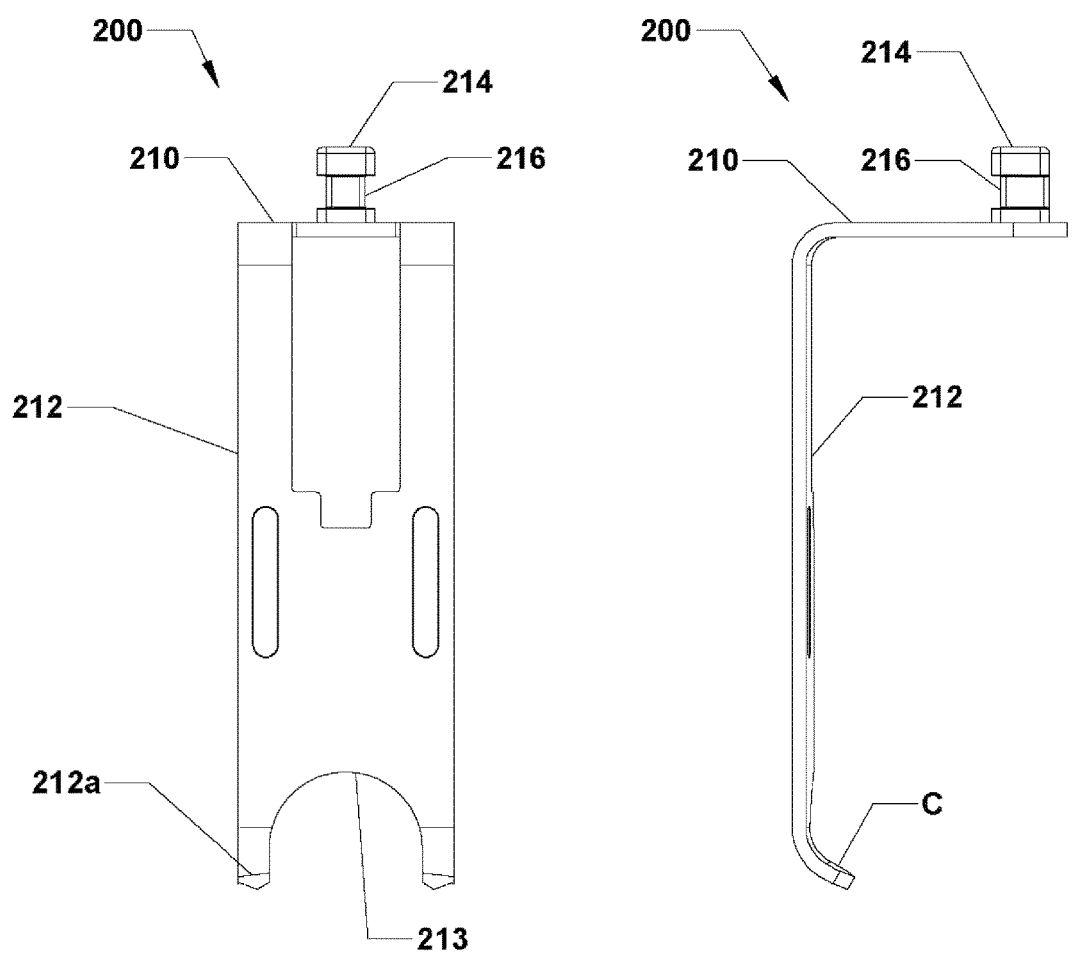
FIG. 4A is a front view of a straight retractor blade in accordance with an embodiment of the present disclosure.
FIG. 4B is a side view of the straight retractor blade of FIG. 4A.

Referring now to FIGS. 4A and 4B, a straight retractor blade 200 includes a planar portion 210 and a blade portion 212 extending, in a different plane, than the planar portion 210. The planar blade portions 210, 212 extend along transverse planes such that the planar and blade portions 210, 212 are substantially orthogonal to each other. The planar portion 210 is configured and dimensioned to engage the back surface 118c (FIG. 1A) of the arm 110, such as in a superposed relationship. The planar portion 210 includes a protruding portion 214 configured and dimensioned to extend into the cavity 111 (FIG. 1A) of the arm 110 through the third opening 111c defined in the back surface 118c of the arm 110. As described in further detail below, the protruding portion 210 includes a groove 216 configured and dimensioned to releasably engage an engaging portion 162 (see e.g., FIG. 6D) of a receiving element 160 of the arm 110. The blade portion 212 includes a distal end 212a having a curvature "C," and defining a recess 213 therein.

As shown in FIGS. 4C-4E, a tapered retractor blade 201 is shown. The tapered retractor blade 201 is substantially similar to the straight retractor blade 200 of FIGS. 4A and 4B, and includes a planar portion 210 including a protruding portion 214 having a groove 216 defined therein, and a blade portion 212' including a distal end 212a' having a curvature "C," and defining a recess 213' therein. The blade portion 212' of the tapered retractor blade 201, however, tapers towards the planar portion 210. While the blade portion 212' is shown as being angled relative to the planar portion 210, it should be understood that the blade portion 212' may be substantially orthogonal to the planar portion 210 as described above with regard to the straight retractor blade 200 of FIGS. 4A and 4B.

FIGS. 5A-5C show an angled retractor blade 202 in accordance with another embodiment of the present disclosure. The angled retractor blade 202 is substantially similar the retractor blades 200, 201 described above with regard to FIGS. 4A-4E. The angled retractor blade 202 includes a planar portion 210" including a protruding portion 214" having a groove 216", and a blade portion 212" including a distal end 212a" having a curvature "C." The blade portion 212" of the angled retractor blade 202 extends along a plane that is angled, but not orthogonal, with respect to the plane along which the planar portion 210" extends. Additionally, the protruding portion 214" is offset at an angle relative to the plane of the planar portion 210". In embodiments, the protruding portion 214" may be disposed at a 30° with respect to the planar portion 210". One of ordinary skill in the art will readily understand that once the protruding portion 214" of the angled retractor blade 202 is engaged with the cavity 111 (see e.g. FIG. 1A) of an arm 110, the blade portion 212" is offset at the angle of the protruding portion 214" relative to a length of the arm 110.

Figure 5D:
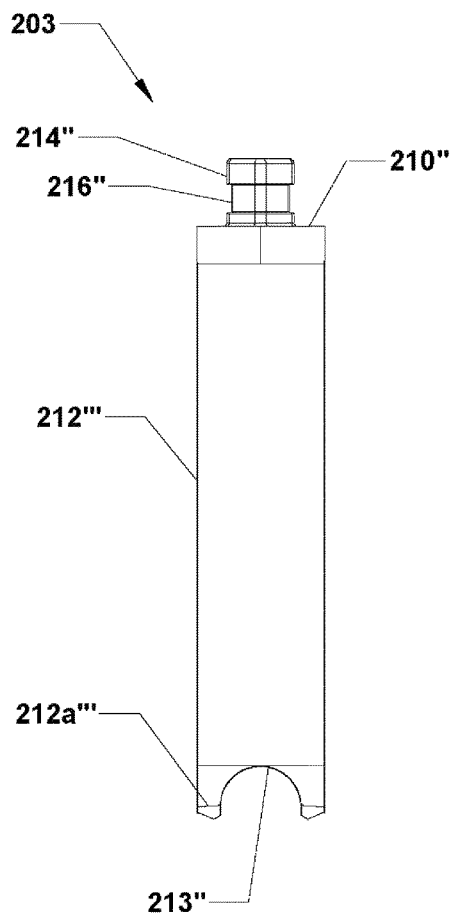
FIG. 5D is a front view of a straight retractor blade in accordance with another embodiment of the present disclosure.
Figure 5E:
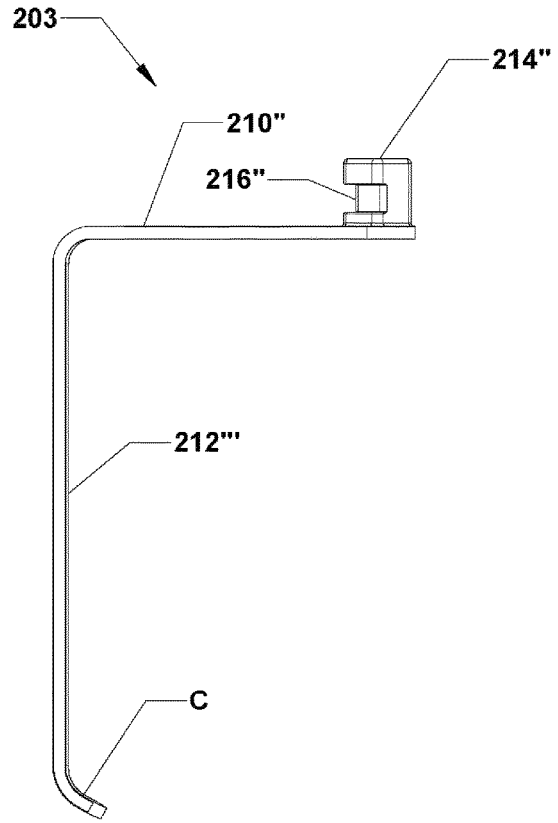
FIG. 5E is a side view of the straight retractor blade of FIG. 5D.

FIGS. 5D and 5E show a straight retractor blade 203 in accordance with yet another embodiment of the present disclosure. The straight retractor blade 203 is substantially similar the angled retractor blade 202 described above with regard to FIGS. 5A-5C, except that the planar portion 210'" and the blade portion 212'" extend along transverse planes that are orthogonal to each other, the protruding portion 214'" is aligned with the planar portion 210'", and a recess 213" is defined in a distal end 212a'" of the blade portion 212'".

Figure 6A:
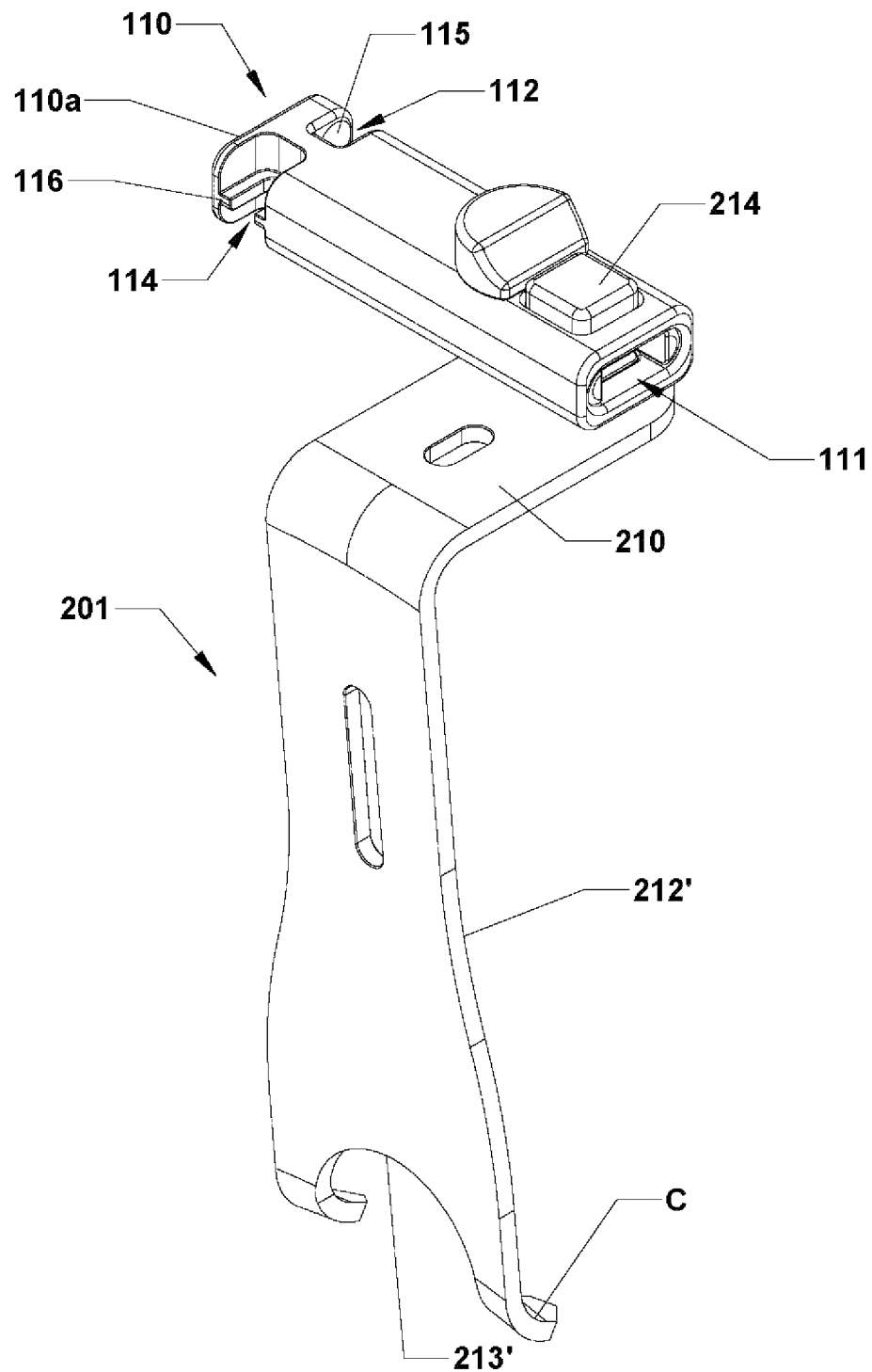
FIG. 6A is a perspective view of the arm of the connector of FIG. 1A releasably secured to the tapered retractor blade of FIG. 4C via a receiving element in accordance with an embodiment of the present disclosure.

As described above, the arm of a connector is configured and dimensioned to receive and support a protruding portion of a retractor blade. As shown, for example, in FIG. 6A, the protruding portion 214 of the retractor blade 201 is received and supported in the 111 cavity, via the third opening 111c (FIG. 6B), of the arm 110 to releasably secure the retractor blade 201 to the arm 110. While the retractor blade shown coupled to the connector is a tapered retractor blade, it should be understood that the retractor blade may be a straight, tapered, or angled retractor blade, such as those shown and described above, among other retractor blades within the purview of those skilled in the art.

Figure 6B:
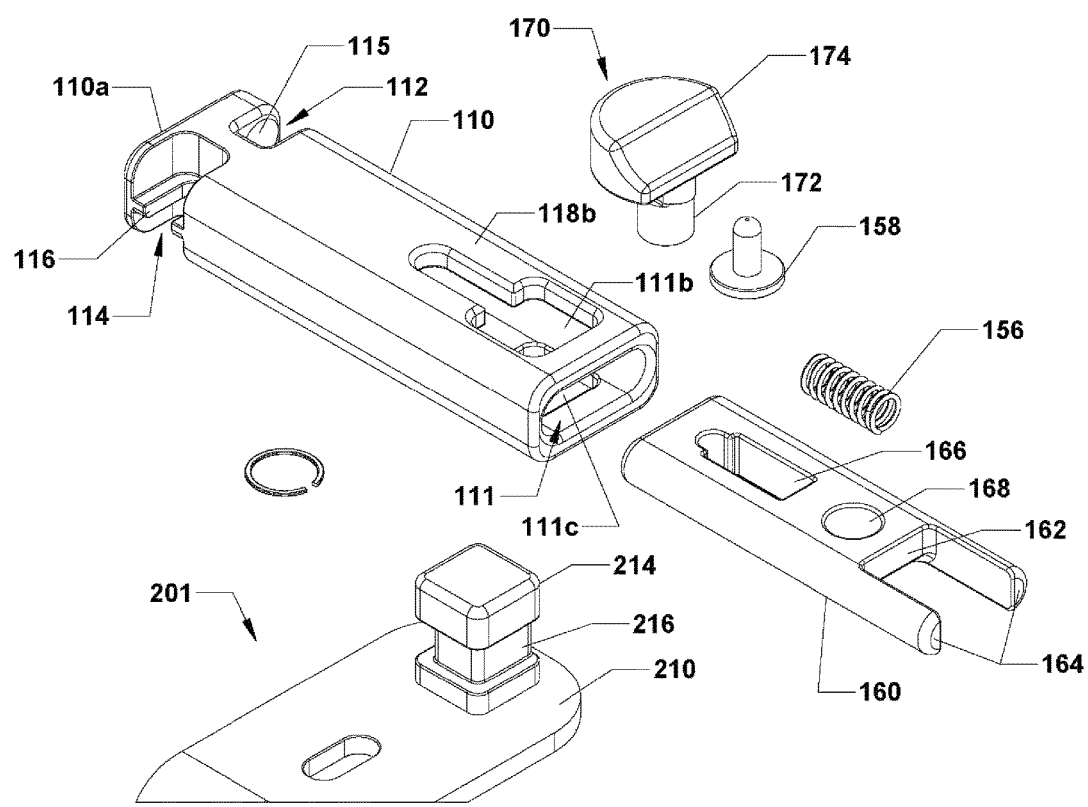
FIG. 6B is an exploded view of the arm and the receiving element of FIG. 6A, with a portion of the tapered retractor blade of FIG. 4C shown separated from the arm.

As shown in FIG. 6B, the cavity 111 of the arm 110 houses a receiving element 160. The receiving element 160 includes an engaging portion or first cavity 162 defined in a forked portion between opposed forks 164. The engaging portion 162 is configured and dimensioned to engage the groove 216 of the protruding portion 214 of the retractor blade 201. In embodiments, the engaging portion 162 includes a beveled edge. The engaging portion 162 can slidably engage the groove 216 defined in the protruding portion 214 to releasably secure the protruding portion 214 of the retractor blade 201 to the arm 110.

The receiving element 160 includes a second cavity 166 configured and dimensioned to engage a spring 156 and a stop 158. The receiving element 160 is biased towards a locked state by the spring 156. In the locked state, the length of the spring 156 is increased, e.g., at its longest length, and the engaging portion 162 is engaged with the groove 216 of the protruding portion 214 of the retractor blade 201. The receiving element 160 includes a third cavity 168 disposed between the first and second cavities 162, 166 that is configured and dimensioned to receive a post 170. The post 170 includes a body 172 and a head 174. The body 172 of the post 170 is configured and dimensioned to extend through the second opening 111b of the arm 110 and into the third cavity 168 of the receiving element 160 such that the head 174 of the post 170 is adjacent the front surface 118b of the arm 110.

Figure 6C:
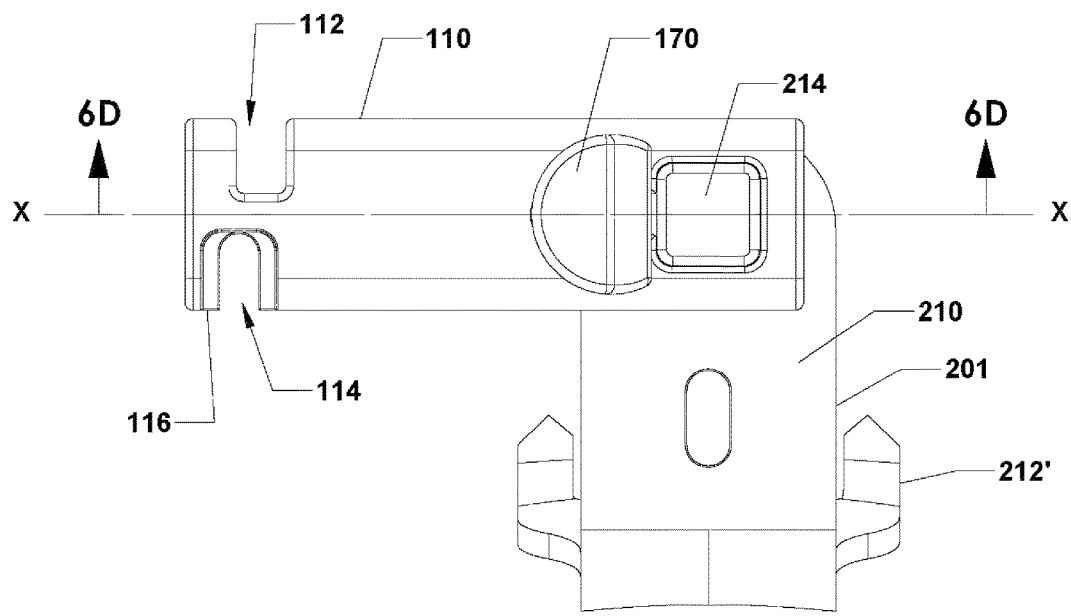
FIG. 6C is a top view of the arm of the connector and the tapered retractor blade of FIG. 4C, with the receiving element in a locked state.
Figure 6D:
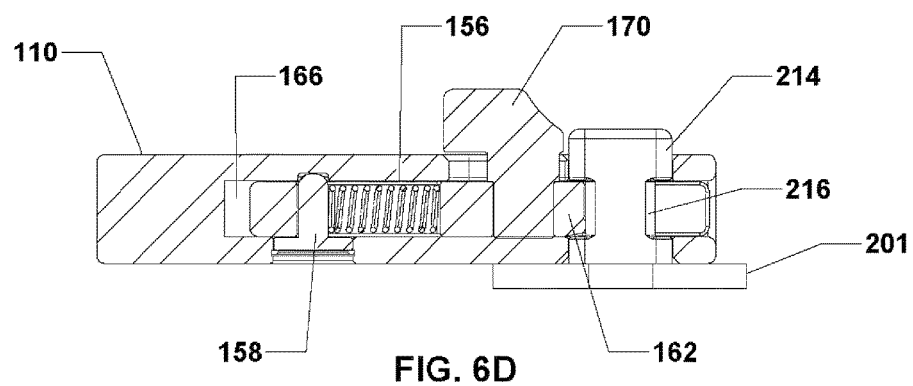
FIG. 6D is a cross-sectional view of the arm of the connector and the tapered retractor blade of FIG. 4C, taken along line 6D-6D of FIG. 6C.
Figure 6E:
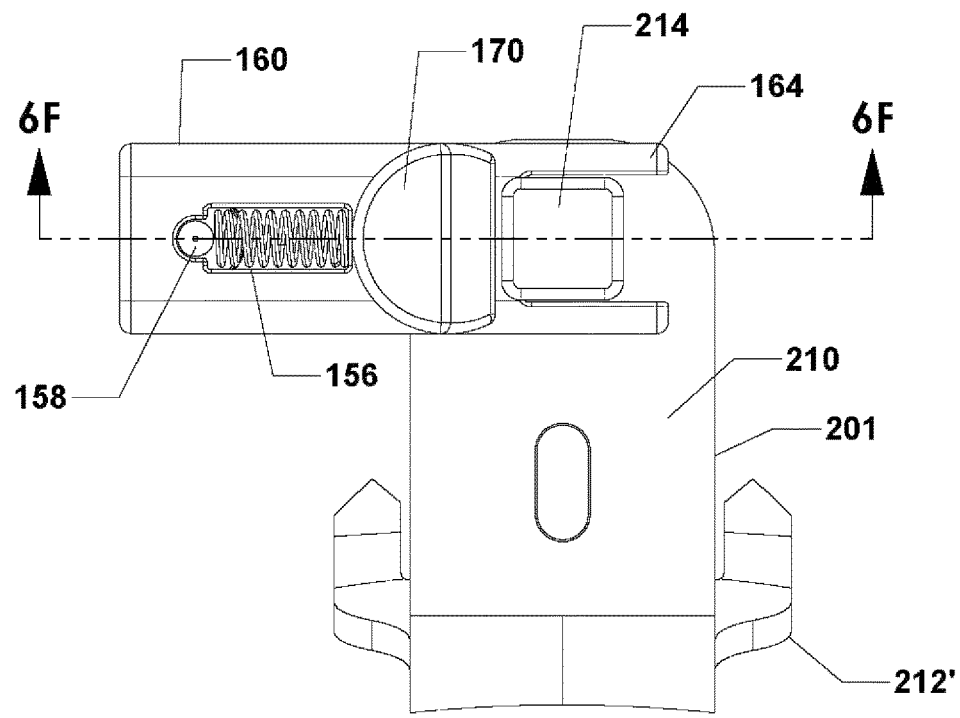
FIG. 6E is a top view of the receiving element, in a locked state, and the tapered retractor blade of FIG. 4C, with the arm of the connector removed.
Figure 6F:
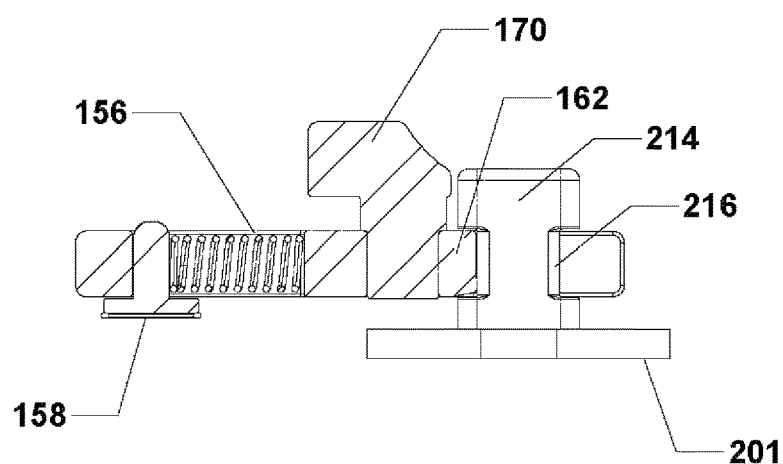
FIG. 6F is a cross-sectional view of the receiving element and the tapered retractor blade of FIG. 4C, taken along line 6F-6F of FIG. 6E.

FIGS. 6C and 6D show the protruding portion 214 of the retractor blade 201 engaged with the engaging portion 162 of the arm 110. The spring 156 is positioned between the stop 158 and an inner wall 166a of the second cavity 166. The engaging portion 162 is engaged with the groove 216 of the protruding portion 214 of the retractor blade 201. As shown in FIGS. 6E and 6F, in both of which the arm 110 has been removed for clear viewing of the receiving element 160, the forked portion of the receiving element 160 (i.e., the space between forks 164) surrounds the protruding portion 214 of the retractor blade 201 on two sides with the engaging portion 162 of the receiving element 160 engaged with the groove 216 of the retractor blade 201. The post 170 is in close proximity to the protruding portion 214 of the retractor blade 201 because the spring 156 biases the receiving element 160 towards the locked state (i.e., spring 156 extends towards its maximum length).

Figure 6G:
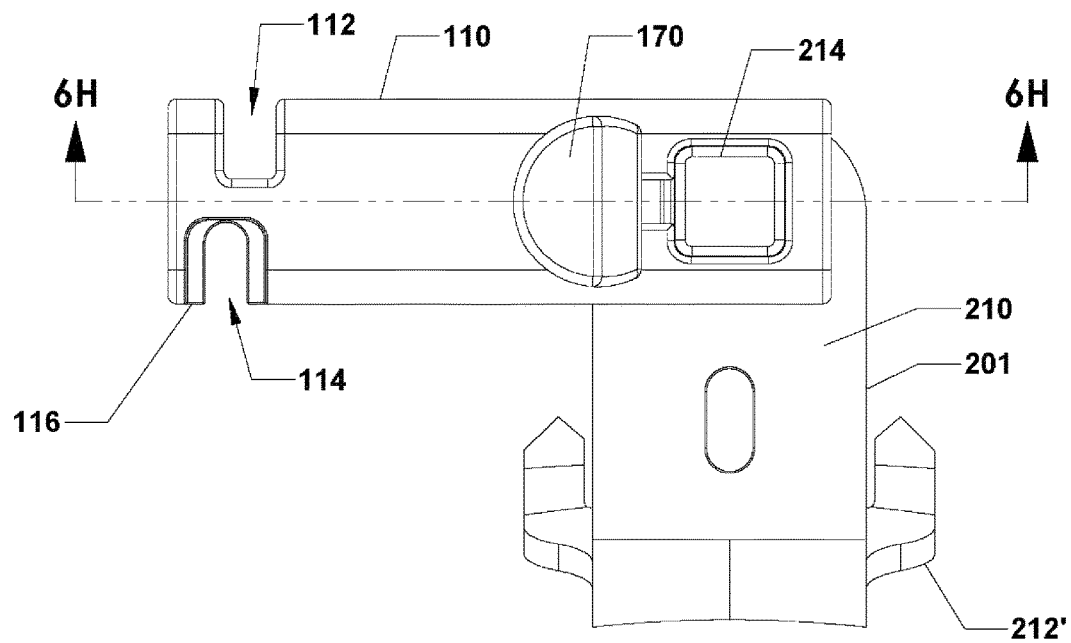
FIG. 6G is a top view of the arm of the connector and the tapered retractor blade of FIG. 4C, with the receiving element in an unlocked state.
Figure 6H:
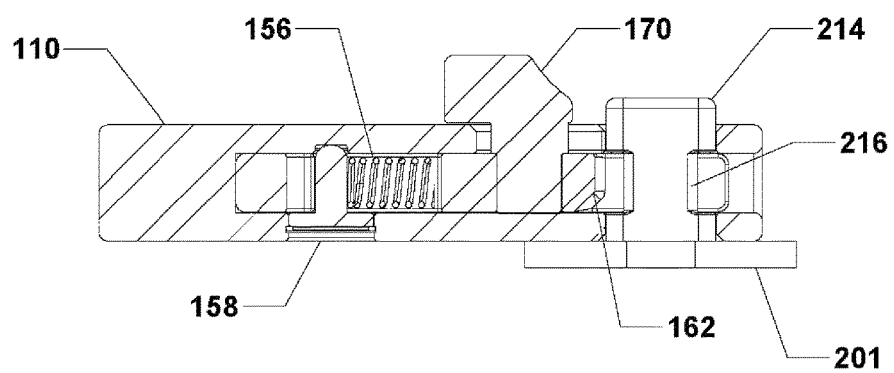
FIG. 6H is a cross-sectional view of the arm of the connector and the tapered retractor blade of FIG. 4C, taken along line 6H-6H of FIG. 6G.
Figure 6I:
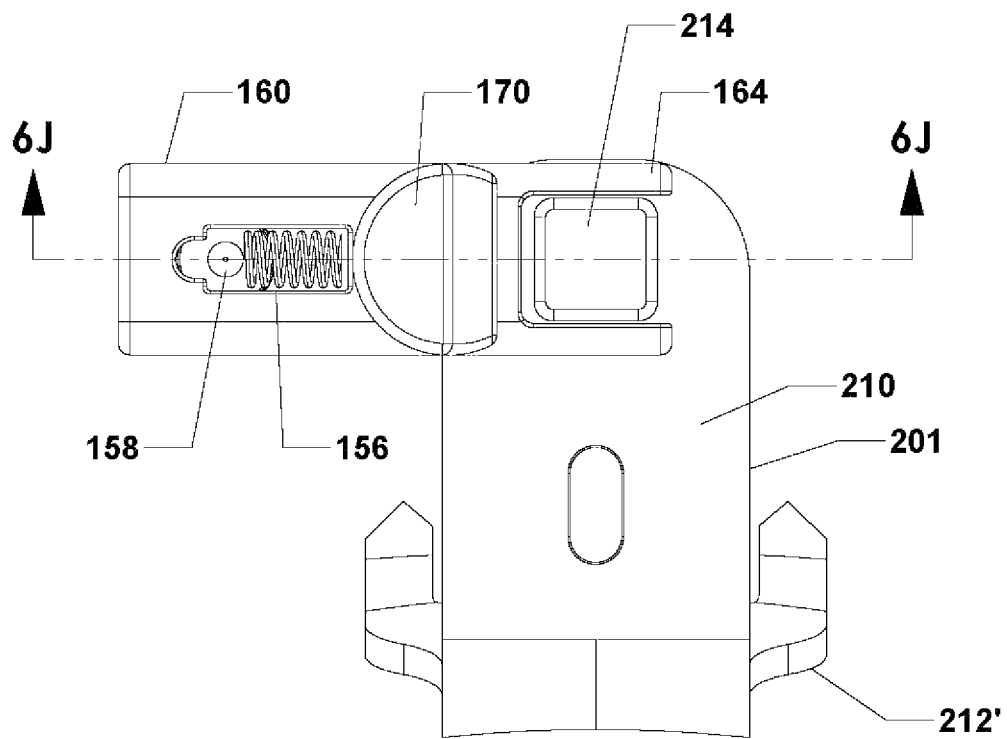
FIG. 6I is a top view of the receiving element, in an unlocked state, and the tapered retractor blade of FIG. 4C, with the arm of the connector removed.
Figure 6J:
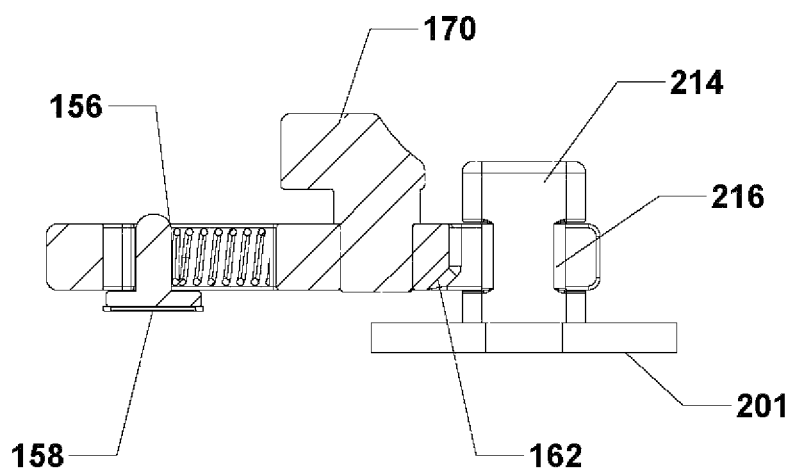
FIG. 6J is a cross-sectional view of the receiving element and the tapered retractor blade of FIG. 4C, taken along line 6J-6J of FIG. 6I.

FIG. 6G and 6H show the engaging portion 162 of the receiving element 160 disengaged from the protruding portion 214 of the retractor blade 201. The post 170 is spaced from the protruding portion 214 of the retractor blade 201 by a distance greater than the distance therebetween when the engaging portion 162 of the receiving element 160 is engaged with the protruding portion 214 of the retractor blade 201 (see e.g. FIG. 6D). A user applies a force to the post 170, which causes the receiving element 160 to compress the spring 156 (i.e., spring compresses towards its minimum length) and receiving element 160 moves towards an unlocked state. With the receiving element 160 in the unlocked state, the length of the spring 156 is shortened relative to the length of the spring 156 when the receiving element 160 is in the locked state because the post 170 acts on the spring 156, and the engaging portion 162 of the receiving element 160 is not engaged with the groove 216 of the protruding portion 214 of the retractor blade 201. As shown in FIGS. 6I and 6J, in both of which the arm 110 has been removed for clear viewing of the receiving element 160, the forked portion of the receiving element 160 surrounds the protruding portion 214 of the retractor blade 201 on two side with the engaging portion 162 of the receiving element 160 disengaged from the groove 216 of the retractor blade 201. The post 170 is separated by a distance from the protruding portion 214 because the spring 156 is compressed and the receiving element is in the unlocked state.

In a method of releasably coupling the retractor blade 201 with the arm 110, the protruding portion 214 of the retractor blade 201 is pushed into the cavity 111 of the arm 110 through the third opening 111c defined in the back surface 118c of the arm 110. The protruding portion 214 forces the engaging portion 162 of the receiving element 160 into an unlocked state (i.e., compressing spring 156) until the protruding portion 214 extends out the cavity 111 through the second opening 111b defined in the front surface 118b of the arm 110. At that moment, the engaging portion 162 enters the locked state (i.e., extending spring 156) thereby releasably securing the protruding portion 214 of the retractor blade 201 within the cavity 111 of the arm 110.

Figures 7A, 7B:
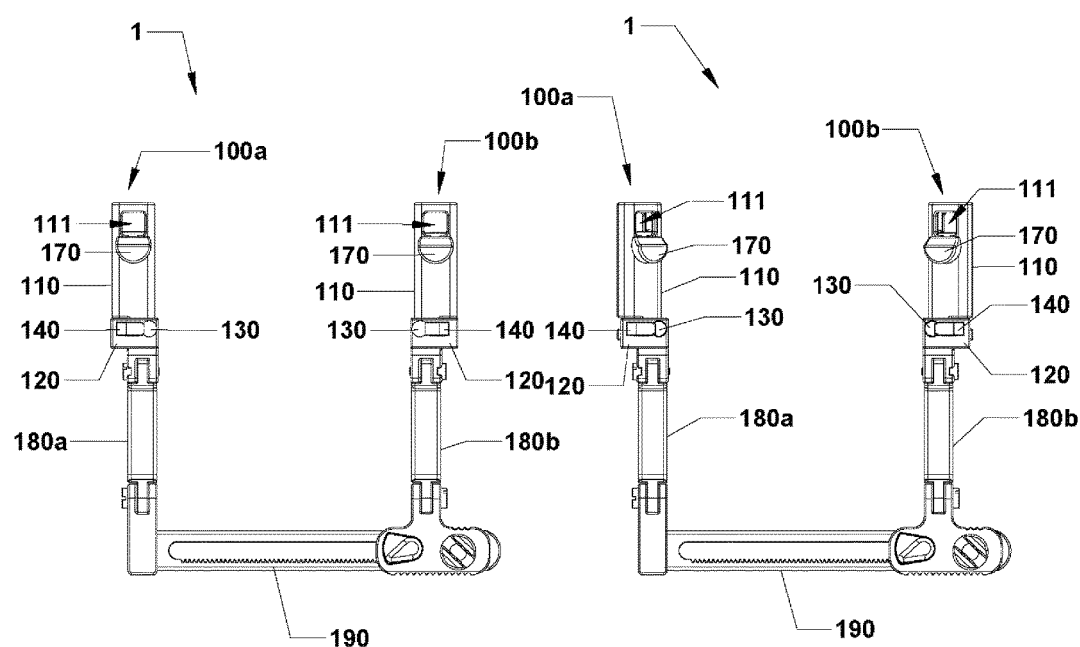
FIG. 7A is a top view of a surgical access system in accordance with an embodiment of the present disclosure, with connectors in a straight or closed position.
FIG. 7B is a top view of the surgical access system of FIG. 7A, with the connectors in an open or angled position.

Referring now to FIGS. 7A and 7B, there is shown a retractor or surgical access system 1 in accordance with an embodiment of the present disclosure. The surgical access system 1 includes a plurality of connectors 100 (designated first and second connectors 100a, 100b), a plurality of supports 180 (designated first and second supports 180a, 180b), and a beam 190. An arm 110 of the first connector 100a is coupled to the first support 180a via a coupling element 120 of the first connector 100a, and an arm 110 of the second connector 100b is coupled to the second support 180b via a coupling element 120 of the second connector 100b. The first support 180a is coupled to the beam 190 and the second support 180b is slidably mounted on the beam 190 such that the second support 180b, and thus the arm 110 of the second connector 100b, can be secured in a plurality of locations relative to the first arm 110 of the first connector 100a which is coupled to the first support 180a.

In embodiments, the first and second connectors 100a, 100b are mirror opposite of each other. For example as shown in FIG. 7A, the coupling element 120, the rod 130, and the ridged slider 140 of the first connector 100a are reversed in location, i.e., mirror opposites, of the coupling element 120, the rod 130, and the ridged slider 140 of the second connector 100b. Such a configuration places the fixation pins 150 (see e.g., FIG. 2B) of the first and second connectors 100a, 100b on lateral sides of the surgical access system 1 allowing the arms 110 of the first and/or second connectors 100a 100b to be rotate about the fixation pins 150 between a closed or straight position as shown in FIG. 7A (see also, e.g., FIGS. 2A and 2B), and an open or angled position as shown in FIG. 7B (see also, e.g., FIGS. 3A and 3B), or at any angle therebetween.

Retractor blades 200 (designated herein as first and second retractor blades 200a and 200b) may be releasably secured to the arms 110 of the first and/or second connectors 100a, 100b of the surgical access system 1 as shown, for example, in FIGS. 8A-9B. While the retractor blades shown coupled to the connectors are straight retractor blades, it should be understood that the retractor blades may be a straight, tapered, or angled retractor blade, such as those shown and described above, and combinations thereof.

The first and second retractor blades 200a, 200b are releasably coupled to the arms 110 of the first and second connectors 100a, 100b, respectively, by engaging the protruding portion 214 of the first and second retractor blades 200a, 200b with the cavities 111 (FIGS. 7A and 7B) of the arms 110, as described above. In FIGS. 8A and 8B, the first and second connectors 100a, 100b are disposed in a straight or closed position such that the planar portions 210 of the first and second retractor blades 200a, 200b are aligned along the same plane and the blade portions 212 are substantially parallel to one another and substantially perpendicular to the beam 190. In FIGS. 9A and 9B, the first and second connectors 100a, 100b are disposed in an opened or angled position. In this configuration, the first and second retractor blades 200a, 200b are separated from one another by an angled distance. In order to open or angle the arms 110 of the first and/or second connectors 100a, 100b, and the attached first and second retractor blades 200a, 200b, a force is applied to the rods 130 of the first and second connectors 100a 100b, as described above, to rotate the arms 110 about the respective fixation pins 150 of the first and second connectors, 100a, 100b. Additionally or alternatively, the arm(s) 110 may be grasped by a user and manually rotated. As seen in FIG. 8B, the first ends 130a of the rods 130 are visible when the connectors 100a, 100b are in the closed position and as seen in FIG. 9B, the second ends 130b of the rods 130 are visible when the connectors 100a, 100b are in the open position. The arms 100, therefore, have been rotated about the fixation pins 150.

Also contemplated for use with the connector 100 and/or surgical access system 1 of the present disclosure is an extension device 300, as shown in FIGS. 10A-10C. The extension device 300 includes a first extension arm 302 having a plurality of projections 304 extending laterally therefrom in spaced relation relative to each other, and a second extension arm 306 also having a plurality of projections 304 extending therefrom. Each projection 304 defines a lumen 305 therethrough that extends perpendicular to the projection 304.

The second extension arm 306 includes first and second ends 306a, 306a each having a protruding portion 308 extending therefrom. Each protruding portion 308 includes a groove 310 defined therein that engages with the engaging portion 162 of the receiving element 160 of the arm 110 of the connector 100. Accordingly, it should be understood that the protruding portions 308 of the extension device 300 is configured to slidingly engage the cavity 111 of the arm 110 and be releasably secured thereto in substantially the same manner as discussed above with regard to the protruding portion of a retractor blade.

The first extension arm 302 is connected to the second extension arm 306 with a plurality of fixation pins 312 and a plurality of torsional springs 314 along the length of the first and second extension arms 302, 306. Each of the plurality of projections 304 of the first extension arm 302 is paired with a projection 304 of the second extension arm 306 to align the lumens 305 of the projections 304. A torsional spring of the plurality of torsional springs 314 is positioned between the paired projections 304 and a fixation pin of the plurality of fixation pins 312 is positioned through paired projections 304 and the torsional spring 314.

Once the first and second extension arms 302 306 are coupled together, a channel 316 is defined therebetween. The second extension arm 306 includes a receiving element 318 extending along the length thereof that is disposed within the channel 316. The channel 316 is configured and dimensioned to releasably secure a plurality of retractor blades thereto, and the receiving element 318 is configured to engage the groove(s) of the protruding portion(s) of the retractor blade(s). It should be understood that the plurality of retractor blades may be straight, tapered, angled, or combinations thereof, as described above.

The extension device 300 may be disposed in a closed position or an open position. The torsional springs 314 bias the extension device 300 to the closed position as shown in FIG. 10A. To open the extension device 300 to the open position, a user applies a force to one or more of the plurality of projections 304 to force the first and second extension arms 302, 306 to rotate about the fixation pins 312 to the open position. Once the extension device 300 is open, the protruding portion(s) of the retractor blade(s) can engage the channel 316.

Figure 11:
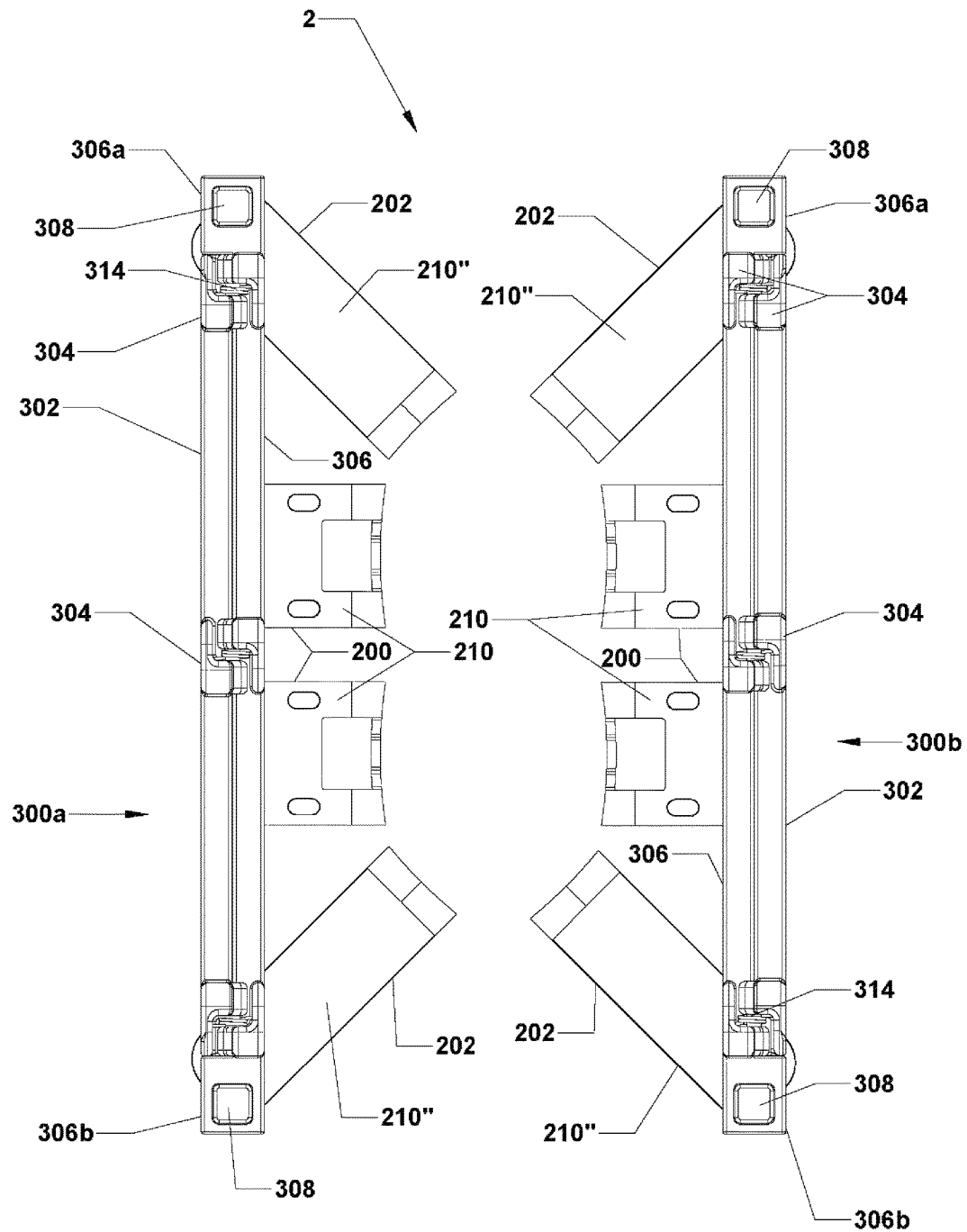
FIG. 11 is a top view of a surgical access system in accordance with another embodiment of the present disclosure.

Referring now to FIG. 11, a retractor or surgical access system 2 is shown including a plurality of extension devices 300 (designated first and second extension devices 300a, 300b). The first and second extension devices 300a, 300b are parallel to one another such that they are a mirror opposite of each other. The surgical access system 2 also includes a plurality of retractor blades, including straight and angled retractor blades 200, 202. It should be understood that any number and combination of retractor blades may be used with the extension devices.

The angled retractor blades 202 are coupled to the first and second ends 306a, 306b of the first and second extension devices 300a, 300b, and the straight retractor blades 200 are coupled to the first and second extension device 300a, 300b between the angled retractor blades 202 about a central portion of the first and second extension devices 300a, 300b. The area defined between the planar portions 210, 210" of the straight and angled retractor blades 200, 202 is substantially oval in shape which can increase the visualization of the surgical field, and minimize stress on the ends of an incision through which the retractor blades 200, 202 of the surgical access system 2 is introduced and placed.

Figures 12A, 12B:
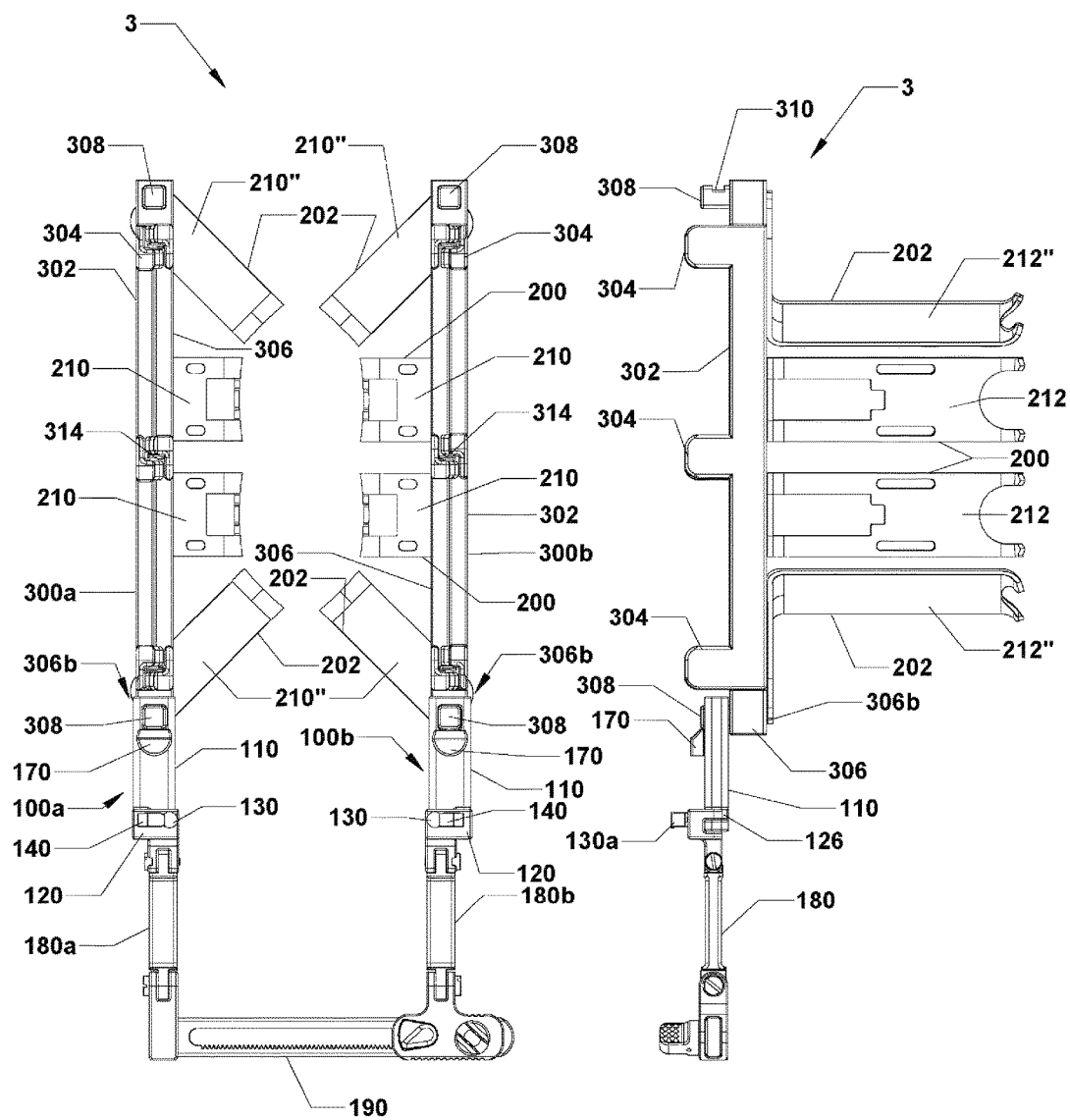
FIG. 12A is a top view of a surgical access system in accordance with yet a further embodiment of the present disclosure.
FIG. 12B is a side view of the surgical access system of FIG. 12A.

FIGS. 12A and 12B show a retractor or surgical access system 3 in accordance with another embodiment of the present disclosure. The surgical access system 3 is substantially similar to the surgical access system 2 of FIG. 11, but further includes a plurality of connectors 100 (designated first and second connectors 100a, 100b), a plurality of supports 180 (designated first and second supports 180a, 180b), and a beam 190.

The second end 306b of the first and second extension devices 300a, 300b are releasably coupled to the first and second connectors 100a, 100b, respectively, by inserting the protruding portion 308 of each of the first and second extension devices 300a 300b into the respective cavity 111 of the arms 110 of each of the first and second connectors 100a, 100b. The engaging portions 162 (see e.g., FIG. 6D) of the respective receiving element 160 of each of the arms 110 then engages with a groove 310 on the respective protruding portion 308 of the first and second extension devices 300a 300b, respectively. The first and second connectors 100a, 100b are coupled to the first and second supports 180a, 180b, respectively, with the first support 180a fixed to the beam 190 and the second support 180b slidably coupled to the beam 190 such that the second support 180b can be secured in a plurality of locations relative to the first support 180a.

It is within the scope of the present disclosure that the plurality of retractor blades 200, 202 are shown in a straight or closed position because the first ends 130a of the rods 130 of the first and second connectors 100a, 100b are visible and accordingly, the arms 110 of the first and second connectors 100a, 100b have not been rotated about their respective fixation pins 150 (see e.g. FIG. 8B).

Figure 13:
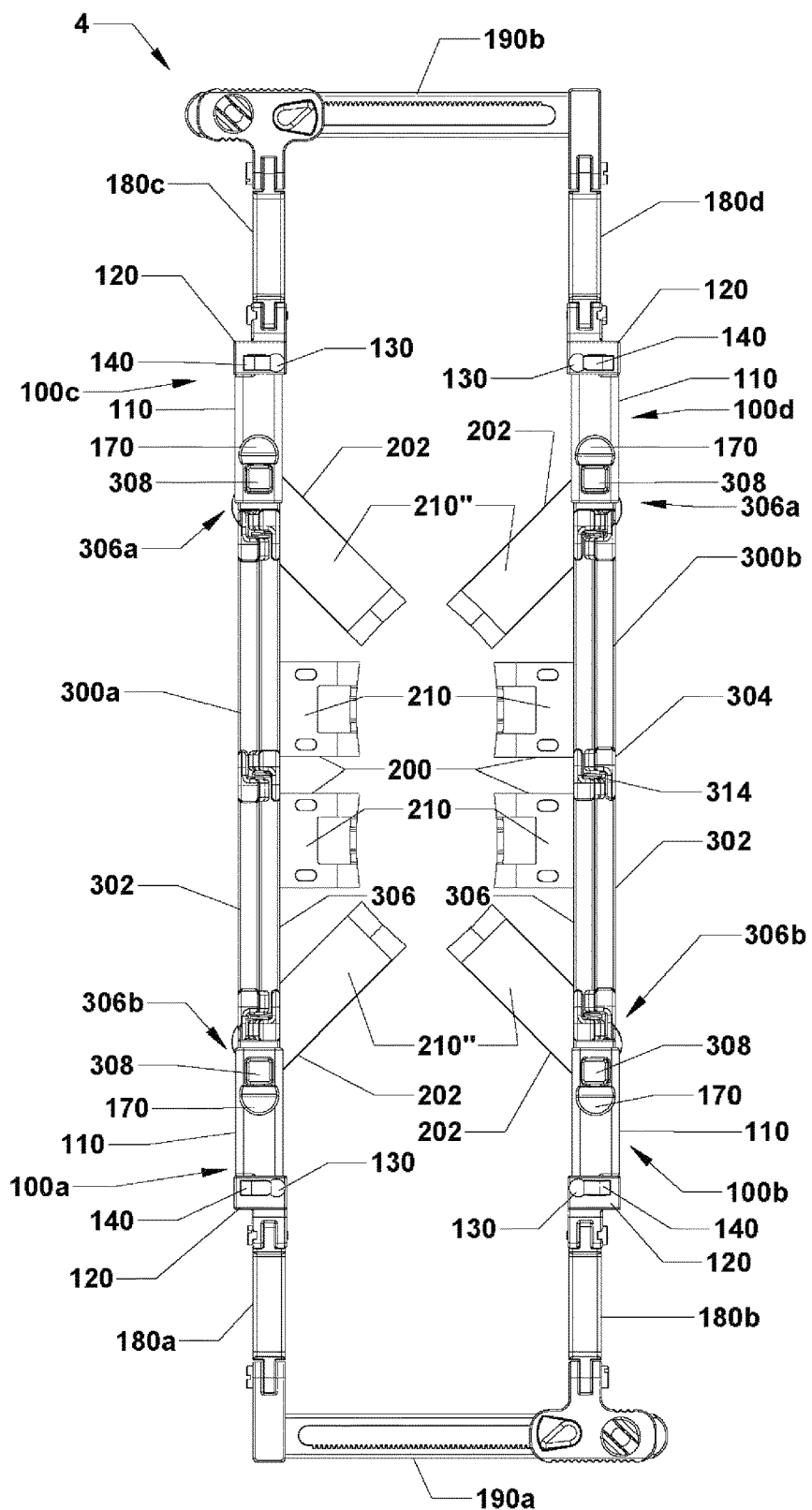
FIG. 13 is a top view of a surgical access system in accordance with an alternate embodiment of the present disclosure.

FIG. 13 shows a retractor or surgical access system 4 in accordance with yet another embodiment of the present disclosure. The surgical access system 4 is substantially similar to the surgical access system 3 of FIGS. 12A and 12B, but further includes third and fourth connectors 100c, 100d, third and fourth supports 180c, 180d, and first and second beams 190a, 190b.

The first ends 306a of the first and second extension devices 300a, 300b are releasably coupled to the third and fourth connectors 100c, 100d, respectively, by inserting the protruding portion 308 of each of the first and second extension devices 300a 300b into the respective cavity 111 of the arms 110 of each of the third and fourth connectors 100c, 100d. The engaging portions 162 (see e.g., FIG. 6D) of the respective receiving element 160 of each of the arms 110 then engages with a groove 310 on the respective protruding portion 308 of the first and second extension devices 300a 300b, respectively. The third and fourth connectors 100c, 100d are coupled to the third and fourth supports 180c, 180d, respectively, with the fourth support 180d fixed to the second beam 190b and the third support 180c slidably coupled to the second beam 190b such that the third support 180c can be secured in a plurality of locations relative to the fourth support 180d.

In embodiments, a user positions the straight and angled retractor blades 200, 202 within an incision of a surgical field. The user releasably secures the protruding portion 214 of each retractor blade 200, 202 into the channels 316 of the first or second extension device 300a, 300b. In particular, the groove 216 of the protruding portion 214 of each retractor blade 200, 202 engages the receiving element 318 of the first or second extension device 300a.

The protruding portions 308 of each of the first and second extension devices 300a, 300b is then releasably secured to the arms 110 of respective first, second, third, and fourth connectors 100a-100d. The user applies a force to insert the protruding portions 308 into the cavity 111 of the arms 110. As described above, the engaging portion 162 of the receiving elements 160 of each of the respective arms 110 engages the groove 310 of the protruding portion 308 of each of the respective first and second extension devices 300a, 300b.

Each arm 110 of the first, second, third, and fourth connectors 100a-100d is connected to first, second, third, and fourth supports 180a-180d, respectively, via the coupling element 120 of each of the first, second, third, and fourth connectors 100a-100d, as described above. The first and fourth supports 180a, 180d are fixed to the first and second beams 190a, 190b, respectively, and the second and third supports 180b, 180c are slidably mounted on the first and second beams 190a, 190b, respectively.

It is contemplated that the extension devices and the secured retractor blades can be moved into an open or angled position when a user applies a force to the rods of the connectors in a manner previously discussed. Additionally, it is contemplated that the extension devices and the secured retractor blades can also be moved into a closed or straight position when a user applies a force to the ridged sliders of the connectors in a manner as also previously discussed.

Figure 14A:
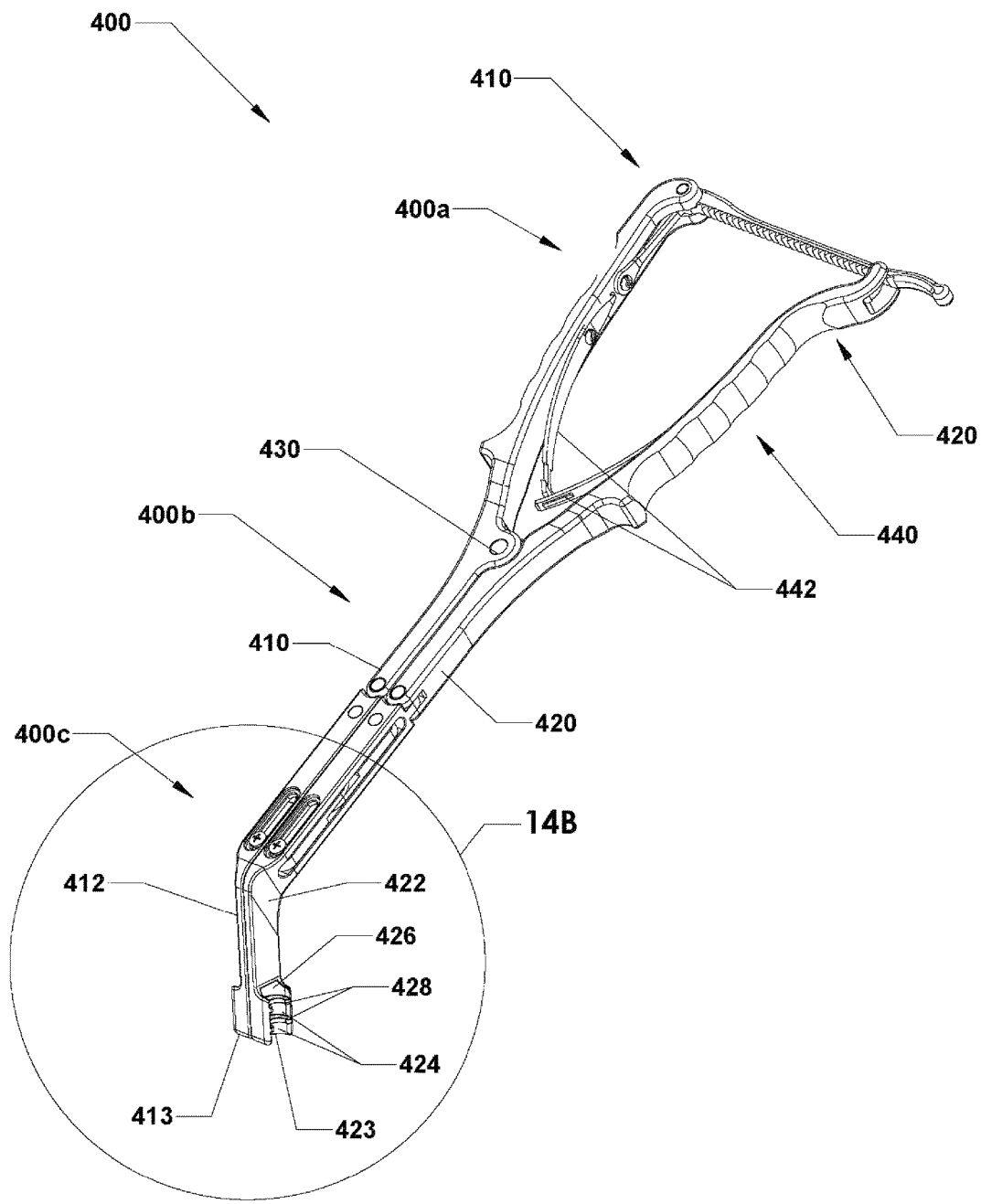
FIG. 14A is a perspective view of a distractor device in accordance with an embodiment of the present disclosure.
Figure 14B:
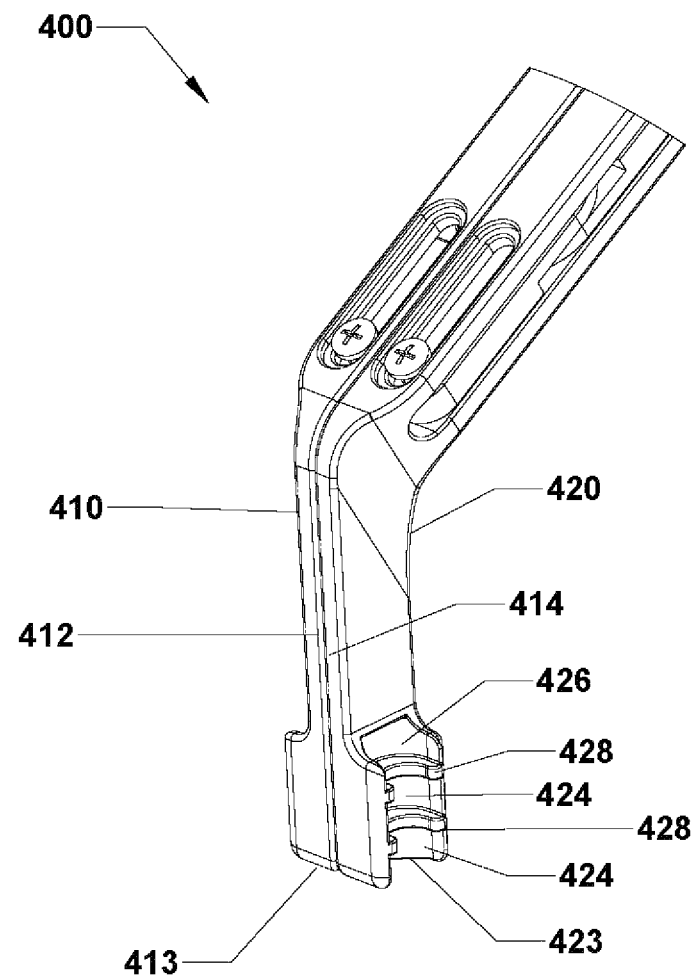
FIG. 14B is an enlarged view of the area of detail of the distractor device of FIG. 14A.

Turning now to FIGS. 14A and 14B, a distractor device 400 is shown. The distractor device 400 includes first and second elongated members 410, 420 connected together via a connection pin 430. The distractor device 400 includes a proximal portion 400a which forms a handle 440 of the distractor device 400. The handle 440 is configured to allow a user to effect movement of at least one of the first and second elongated members 410, 420 relative to the other. In use, a force may be applied to the handle 440 to cause the first and second elongated members 410, 420 to move from a closed position, as shown in FIG. 14A, to an open position, as discussed in further detail below. The handle 440 may include a biasing mechanism 442 positioned between the first and second elongated members 412, 422 in the proximal portion of the distractor device 400 which biases the first and second elongated members 410, 420 to the open or closed positions.

The distractor device 400 includes a central portion 400b and that extends along a longitudinal axis "X" (FIG. 16A) of the distractor device 400, and a distal portion 400c pivotably connected to the central portion 400b.

Each of the first and second elongated members 410, 420 includes a flat portion 412, 422 on lateral sides of the distal portion 400c, and a partial lumen 413, 423 extending substantially perpendicularly from the flat portions 412 422. The flat portions 412, 422 are substantially parallel to each other and abut each other when the distractor device 400 is in a closed position. The partial lumens 413, 423 extend at least partially along a length of its corresponding first or second elongated member 410, 420.

While only the partial lumen 423 of the second elongated member 420 is shown in FIGS. 14A and 14B, it should be understood that the partial lumen 413 of the first elongated member 410 is identical thereto. The partial lumens 413, 423 include a plurality of detents 414, 424 extending from an inner wall 416, 426 of the partial lumens 413, 423, respectively, in spaced relation relative to each other. In embodiments, the partial lumens 413, 423 include one or more detents 414, 424, in some embodiments, the partial lumens 413, 423 include two or more detents 414, 424, and in certain embodiments, the partial lumens 413, 423 include three or more detents 414, 424. Each detent of the plurality of detents 414, 424 is configured and dimensioned to releasably secure a protrusion 516 (see e.g., FIG. 15) of a pin 500, as described in further detail below.

The detents 414, 424 are separated from each other by a ledge 418, 428 extending along the inner wall 416, 426 of the partial lumens 413, 423. It should be understood that any number of detents 414, 424 and ledges 418, 428 may be disposed in the partial lumens 413, 423 so long as they are in an alternating pattern of, for example, detent, ledge, detent, ledge, and detent. In embodiments, the ledge 418, 428 is continuous along the inner wall 416, 426 of the partial lumens 413, 423. In some embodiments, the ledge 418, 428 is non-continuous along the inner wall 416, 426 of the partial lumens 413, 423.

The height of each detent 414, 424 from one ledge 418, 428 to another ledge 418, 428 is variable and is based, in part, upon the height of each protrusion 516 (see e.g., FIG. 15) of a pin 500. At a minimum, the height of a detent 414, 424 from one ledge 418, 428 to another ledge 418, 428 is the same as the height of a protrusion 516 of a pin 500. The distance of a detent 414, 424 from one ledge 418, 428 to another ledge 418, 428 should be at least sufficient to releasably secure the protrusion 516 of the pin 500, and optionally a gap 517, which is disposed above and/or below the protrusion 516. As specifically shown in FIG. 16E, the gap 517 of the pin 500 should be enough to ensure the protrusion 516 is releasably secured within the detent 414, 424 of the first or second extensions arms 410, 420, and provide some additional space for small movements of the distractor device 400. However, the gap 517 should not be so great as to allow the protrusion 517 to become dislodged or separated from the detent 414, 424 and/or allow for large vertical movements of the distractor device 400 during use.

In embodiments, the distractor device 400, in its natural or biased state, is in the closed position. In the closed position, each of the flat portions 412, 422 of the first and second elongate members 410, 420 are substantially parallel to, and abut, each other. When a force is applied to the handle 440 (i.e., handle portions move towards each other), the first and second elongated members 410, 420 move from the closed position to the open position (i.e., away from each other). In the open position, the flat portions 412, 422 of the first and second elongate members 410 420 remain parallel to each other but are separated by a lateral distance. The separated distance can be increased by increasing the force on the handle 440 of the distractor device 400. When the force on the handle 440 is released, the first and second elongated members 410, 420 move toward each other to reduce the separated distance until the first and second elongate members 410, 420 return to the closed position, such as via the biasing mechanism 442 which can force each of the first and second elongated members 410, 420 towards each other (i.e., forces the first and second elongated members 410, 420 to the closed position).

Figure 15:
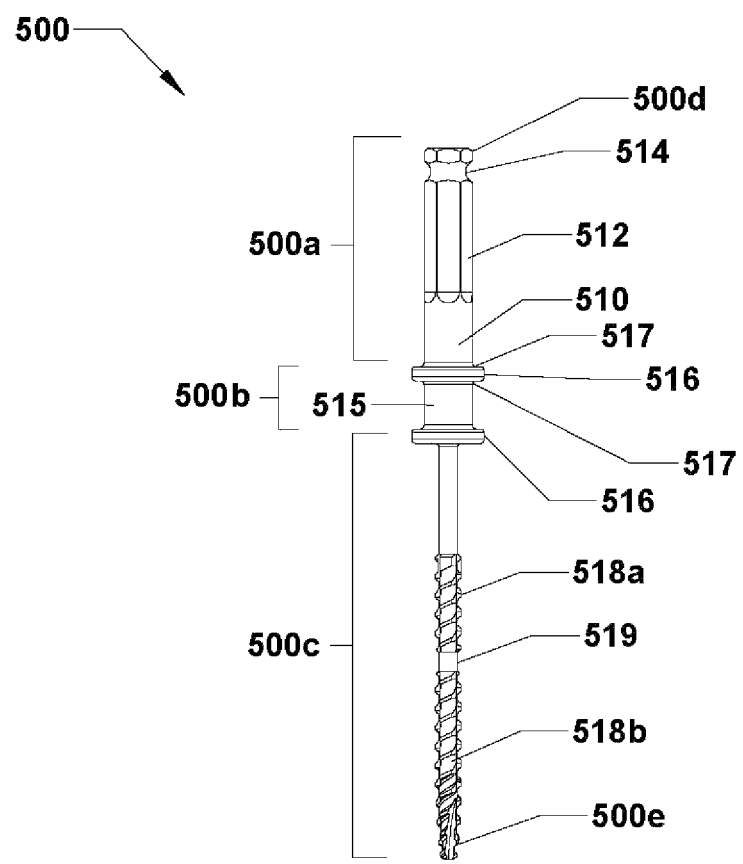
FIG. 15 is a front view of a pin in accordance with an embodiment of the present disclosure.

An exemplary pin 500 for use with the distractor device 400 is shown in FIG. 15. The pin 500 includes a proximal section 500a, an intermediate section 500b, and a distal section 500c. The proximal section 500a includes a shaft 510 at least partially cut with hexagonal facets 512 along its length. The hexagonal facets 512 terminate at a circumferential groove 514. The circumferential 514 is located near a proximal end 500d of the pin 500. The hexagon facets 512 and/or the circumferential groove 514 can increase a friction fit with a device to insert the pin 500 into a vertebral body.

The proximal and distal sections 500a, 500c are separated by the intermediate section 500b. The intermediate section 500b includes a plurality of protrusions 516 disposed in spaced relation relative to each other. In embodiments, the intermediate section 500b includes one or more protrusions 516, in some embodiments, the intermediate section 500b includes two or more protrusions 516, and in certain embodiments, the intermediate section 500b includes three or more protrusions 516. In embodiments, each protrusion of the plurality of protrusions 516 is continuous around the circumference of the pin 500. In some embodiments, the plurality of protrusions 516 are non-continuous around the circumference of the pin 500.

The protrusions 516 are separated from each other by an interval 515. One of ordinary skill in the art can appreciate that any number of protrusions 516 and intervals 515 can be configured so long as they are in an alternating pattern of, for example, protrusion, interval, and protrusion.

Each protrusion of the plurality of protrusions 516 is configured and dimensioned to releasably engage a detent 414, 424 on the distractor device 400 (FIGS. 1A, 1B). It should be understand that the plurality of protrusions 516 can be any shape or in any pattern so long as they are configured to releasably secure the pin 500 to the plurality of detents 414, 424 (FIG. 1A, 1B) of the distractor device 400.

The height of a protrusion 516 can vary and be based, in part, upon the height of each detent 414, 424 of a distractor device 400. At a maximum, the height of a protrusion 516 is less than the height of a detent 414, 424 so that the protrusion and the detent 414, 424 are snugly releasably secured together. As shown in FIG. 16E, the height of the protrusion 516 should be at least sufficient to releasably secure the protrusion 516, and optionally a gap 517 disposed above and/or below the protrusion 516. The gap 517 ensures the protrusion 516 is releasably secured within the detent 414, 424 and provide some additional space for small movement of the distractor device 400. The gap(s) 517, however, should not be so great as to allow the protrusion 516 to become unsecured from the detent 414, 424 and/or allow for large vertical movements of the distractor device 400 during use.

The distal section 500c of the pin 500 includes a first threaded portion 518a and a second threaded section 518b longitudinally spaced from each other and separated by a non-threaded gap 519. The second threaded section 518b terminates at a threaded tapered distal end 500e. The gap 519 may be a visual marker for a user to measure the depth of insertion of the pin 500 into a vertebral body. In embodiments, the visual marker may be in the form of a color, change of material, or change in pattern. In embodiments, the pin 500 includes a plurality of visual markers. In some embodiments, each visual marker may be in the form of a color or a pattern. For example, a first pre-determined color may indicate that the pin 500 is at a first depth into the vertebral body, a second pre-determined color can indicate that the pin 500 is at a second depth into the vertebral body, and so on.

The pin 500 may have a length of from about 3 inches to about 4 inches. In embodiments, the pin 500 has a length from about 3.2 inches to about 3.8 inches. In some embodiments, the pin 500 has a length of from about 3.4 inches to about 3.6 inches, and in certain embodiments, the pin 500 has a length of about 3.5 inches.

Figure 16A:
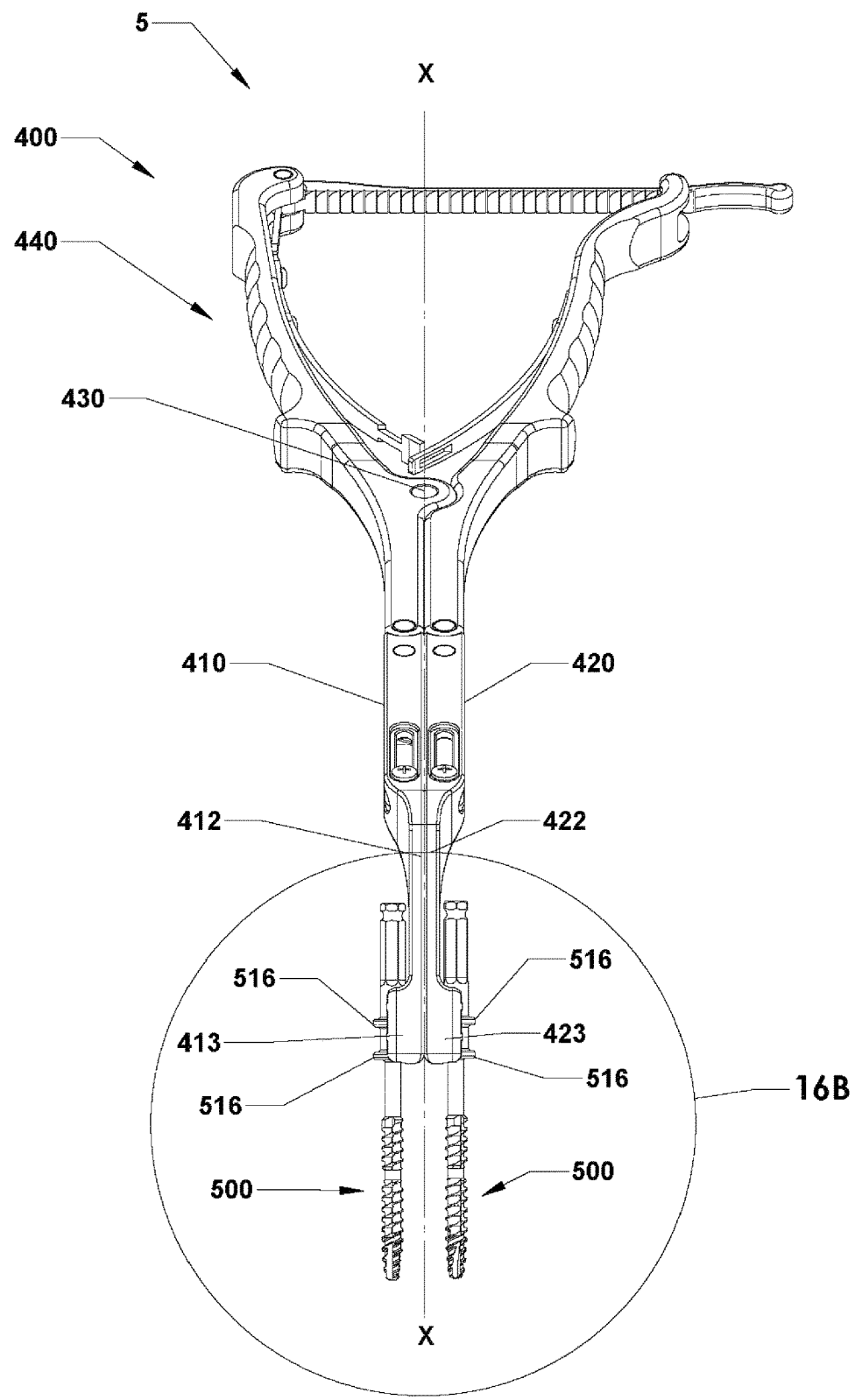
FIG. 16A is a front perspective view of a surgical distraction system with the distractor device of FIG. 14A coupled to pins of FIG. 15 in accordance with an embodiment of the present disclosure.
Figure 16B:
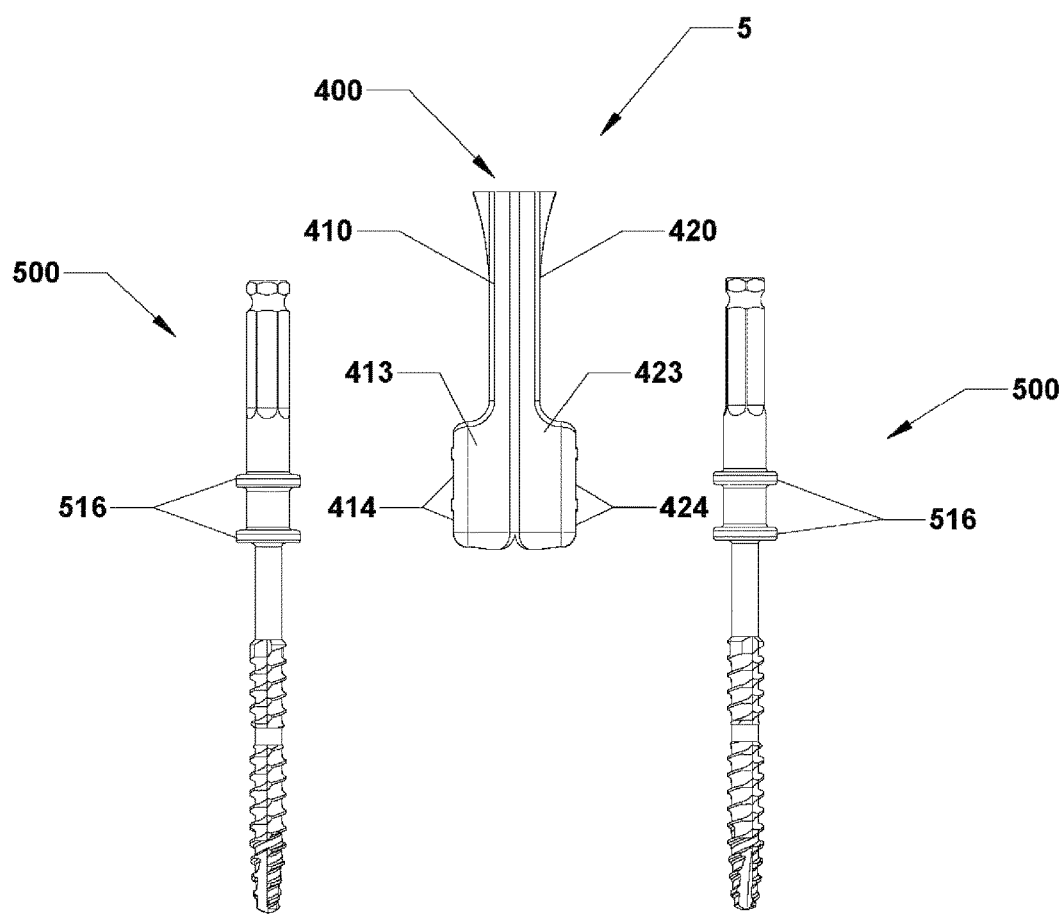
FIG. 16B is an enlarged view of the area of detail of FIG. 16A showing the pins separated from the distractor device.
Figure 16C:
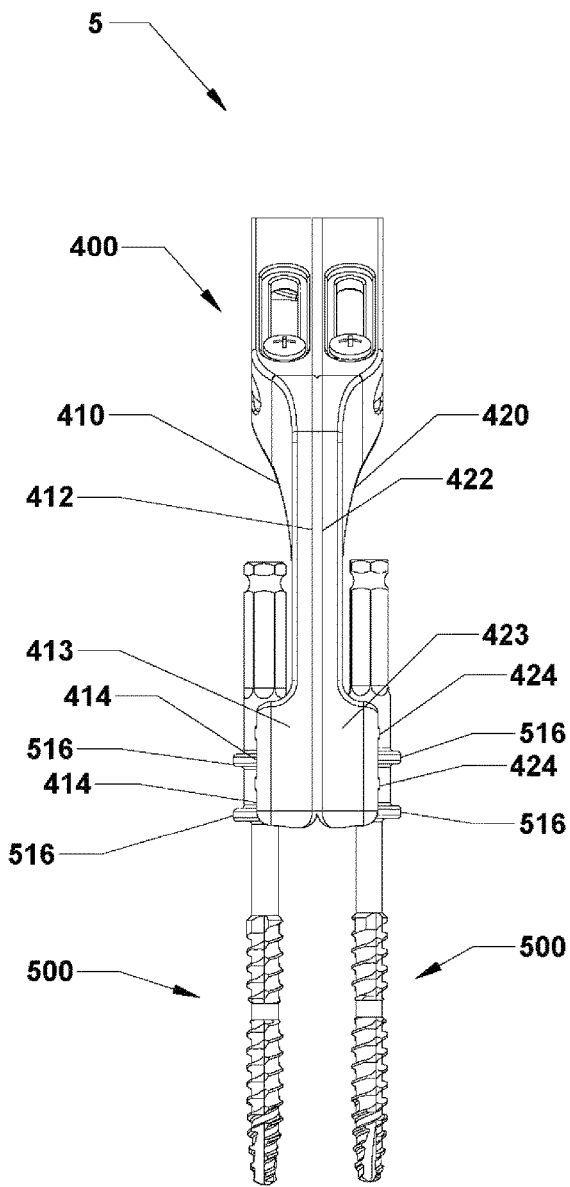
FIG. 16C is a front end view of the surgical distraction system of FIG. 16A.
Figure 16E:
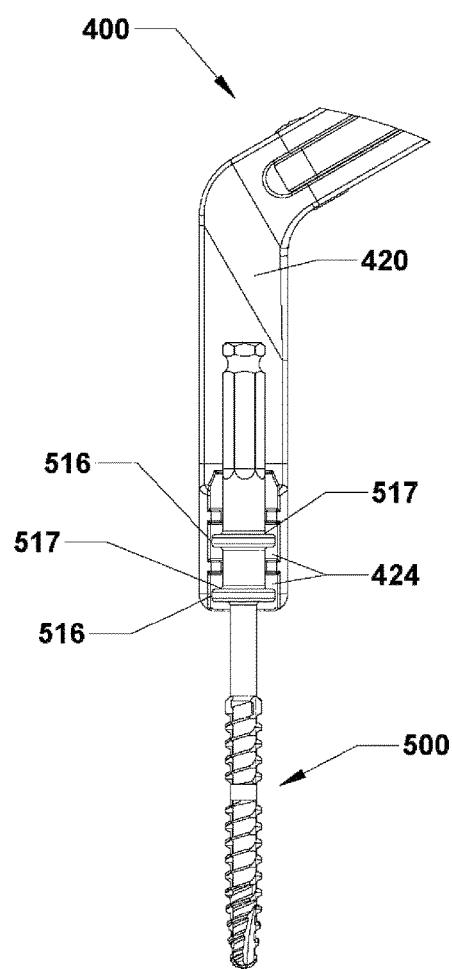
FIG. 16E is an enlarged side view of the area of detail of FIG. 16D showing a distal portion of the surgical distraction system.
Figure 16D:
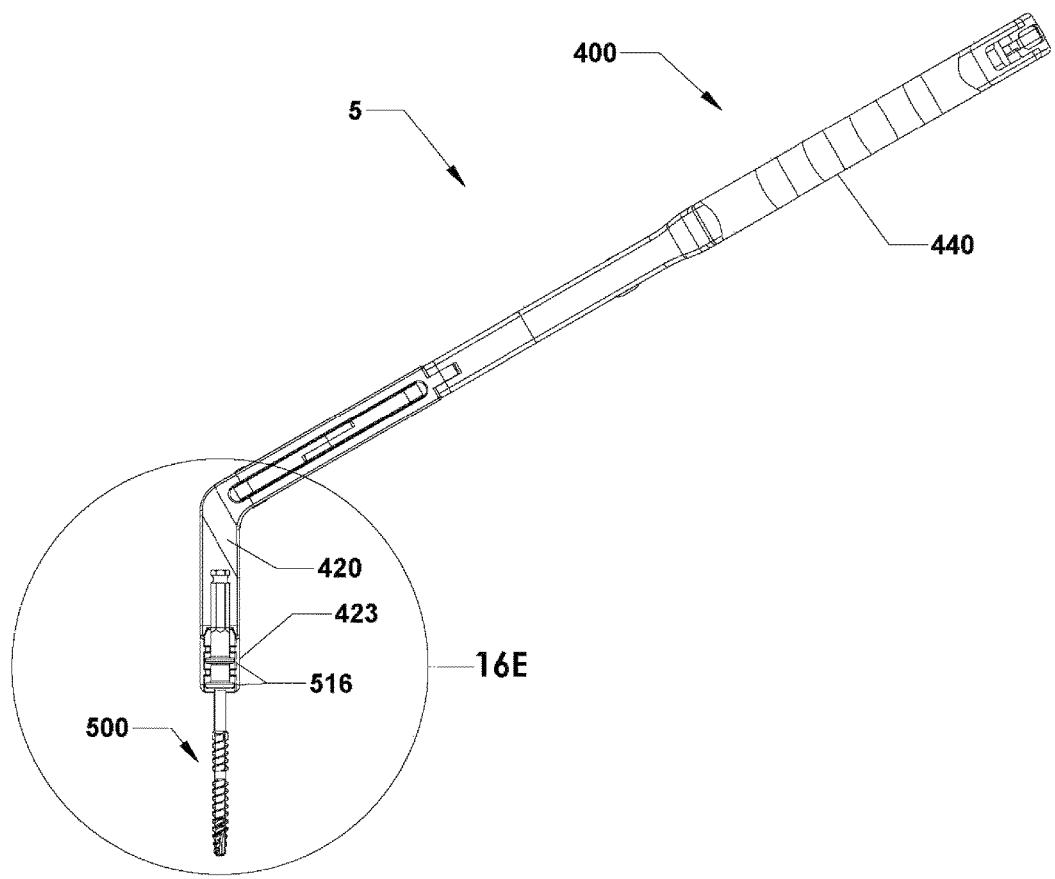
FIG. 16D is a side view of the surgical distraction system of FIG. 16A.

As shown in FIGS. 16A-16E, a surgical distraction system 5 includes a distractor device 400 and a plurality of pins 500. In a method of use, the pins 500 are placed in adjacent vertebral bodies, and the distractor device 400 is positioned between the pins 500, as shown in FIG. 16A. The plurality of detents 414, 424 of the first and second elongate members 410, 420 are brought into contact with the plurality of protrusions 516 of the pins 500 to releasably secure the distractor device 400 to the pins 500, as shown in FIGS. 16B-16E. A force can be applied to the handle 440 of the distractor device 400 to move the first and second elongated members 410, 420 of the distractor device 400 from a closed position to an open position to assist in releasably securing the plurality of detents 414, 424 to the plurality of protrusions 516 of the pins 500.

After attaching the pins 500 to the distractor device 400, the pins 500 are substantially parallel to one another and the distractor device 400 is disposed in the closed position. The handle 440 of the distractor device 400 may then be manipulated (e.g., by squeezing the first and second elongated members 410, 420 towards each other) to create a separation between the first and second adjacent vertebral bodies. Squeezing the handle 440 applies a distraction force to the adjacent vertebral bodies by moving the pins 500, which remain substantially parallel to each other when in an open position, and thus the vertebral bodies away from each other and creating a space, or separation, between the adjacent vertebral bodies. One or ordinary skill in the art will readily understand the need for the pins 500 to remain substantially parallel to each other in a method for separating vertebral bodies.

An intervertebral disc located between the adjacent vertebral bodies may then be removed. Once the intervertebral disc is removed, an implant can be inserted. Thereafter, the handle 440 may be further manipulated to remove the distraction force, and the distractor device 400 may be removed with the pins 500 from the adjacent vertebral bodies.

Referring now to FIGS. 17A-17C, a connector 600 in accordance with another embodiment of the present disclosure is shown. The connector 600 includes an arm 610, a coupling element 620, and a gear assembly 630 having a first gear 632 and a second gear 634. The arm 610 is configured and dimensioned to receive and support the second gear 634, and the coupling element 620 is configured and dimensioned to receive and support the first gear 632. The coupling element 620 is coupled to the arm 610 with the first and second gears 632, 634 meshingly engaged with each other such that rotation of the first gear 632 results in rotation of the second gear 634 which, in turn, pivots the arm 610 with respect to the coupling element 620, as will be described in detail hereinbelow.

The arm 610 includes a first end portion 610a and a second end portion 610b. The second gear 634 is non-rotatably coupled to the first end portion 610a of the arm 610, and the second end portion 610b includes a cavity 611 defined therein. The cavity 611 is configured and dimensioned to house the receiving element 160 (see FIG. 6B) which, in turn, is configured and dimensioned to engage the protruding portion 214 (see FIG. 6A) of the retractor blade 201, as described above. Similar to the cavity 111 of the arm 110 of FIGS. 6A and 6B, the cavity 611 is open at a first opening (not shown) defined in a proximal surface 612a of the arm 610, a second opening (not shown) defined in a front surface 612b of the arm 610, and a third opening 611c defined in a back surface 612c of the arm 610.

The coupling element 620 includes a body portion 622 having a cavity 623 defined therein that is configured and dimensioned to receive and support the first gear 632. An opening 625 of the cavity 623 is defined in a front surface 624a of the coupling element 620, and a plate 626 is secured to a back surface 624b of the coupling element 620 via a fastener 627, such as a screw. Retaining features 628 extend from the body portion 622 of the coupling element 620 for coupling with a support 181 (see e.g., FIG. 18A).

The first gear 632 is in the form of a screw and includes a head portion 636a having a recessed end 637 configured to mate with a driving instrument (not shown) and an elongated threaded body portion 636b terminating at a distal end 636c. The recessed end 637 may be a recessed hex feature, e.g., hexagonal or hexolobular in shape, or any other suitable configuration that is engageable with a suitable driving instrument to enable the driving instrument to control rotation of the first gear 632. The first gear 632 is rotatably disposed within the cavity 623 of the coupling element 620 such that the recessed end 637 of the head portion 636a is accessible through the opening 625 of the coupling element 620, and the distal end 636c abuts an inner surface of the plate 626. In embodiments, the first gear 632 is a worm screw.

The second gear 634 is in the form of a wheel and includes a rounded body portion 638a having a toothed outer surface 638b. The second gear 634 is non-rotatably coupled to the first end portion 610a of the arm 110 such that the toothed outer surface 638b meshingly engages the elongated threaded body portion 636b of the first gear 632. It should be understood that the toothed outer surface 638b of the second gear 634 has a pitch and shape to mate with the elongated threaded body portion 636b of the first gear 632 allowing for fine angular adjustments of the arm 610 relative to the coupling element 620. In embodiments, the second gear 634 is a worm wheel.

Figure 18A:
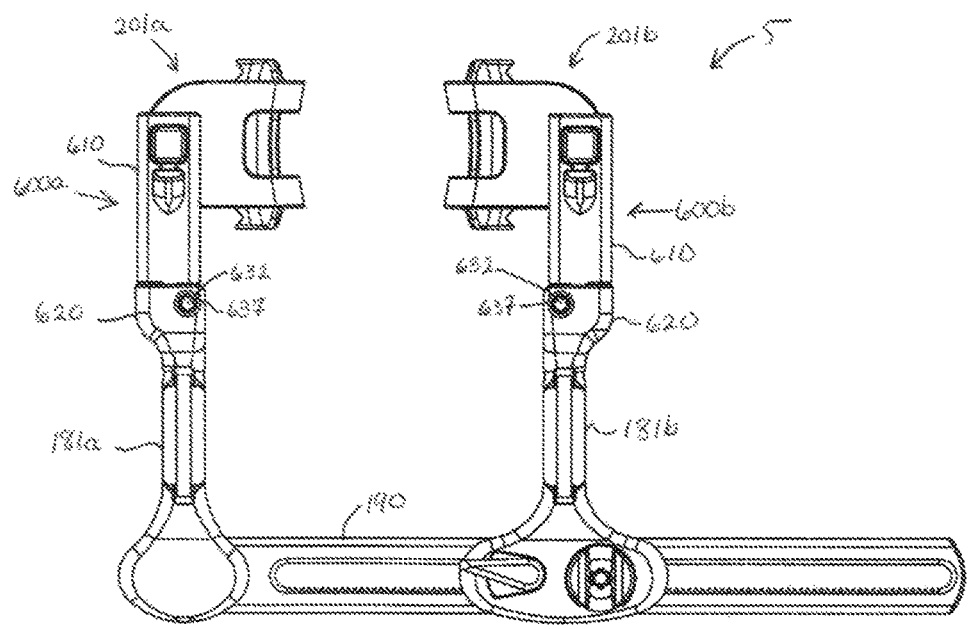
FIG. 18A is a top view of a surgical access system in accordance with an embodiment of the present disclosure, with connectors in a straight position.
Figure 18B:
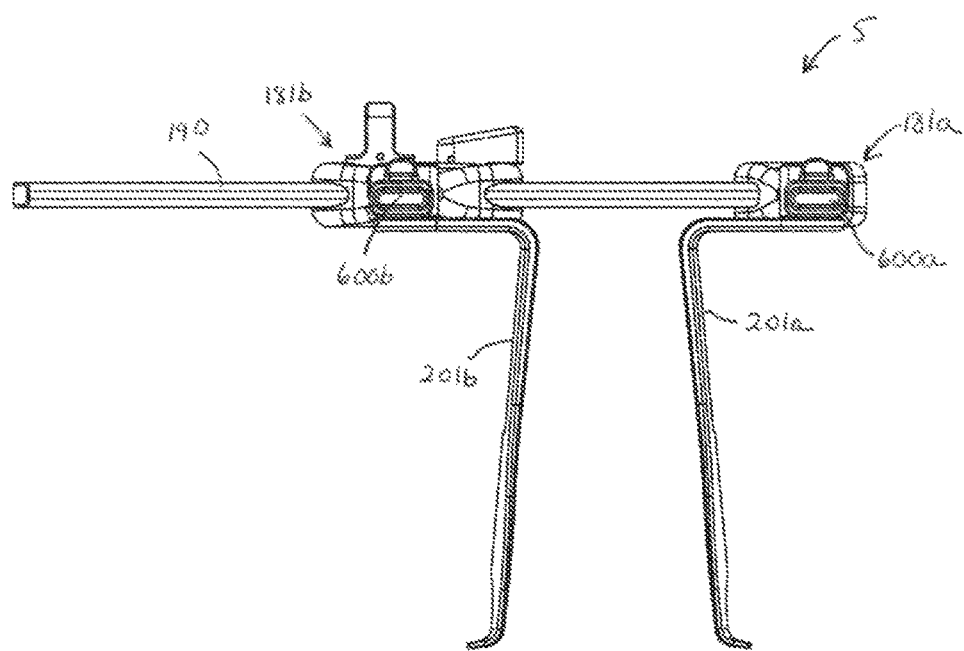
FIG. 18B is a side view of the surgical access system of FIG. 18A.

Turning now to FIGS. 18A and 18B, there is shown a retractor or surgical access system 5 in accordance with an embodiment of the present disclosure. The surgical access system 5 includes a plurality of connectors 600 (designated first and second connectors 600a, 600b), a plurality of supports 181 (designated first and second supports 181a, 181b), and a beam 190. The first connector 600a is coupled to the first support 181a via the coupling element 620 of the first connector 600a, and the second connector 600b is coupled to the second support 181b via the coupling element 620 of the second connector 600b. The first support 181a is coupled to the beam 190 and the second support 181b is slidably mounted on the beam 190 such that the second support 181b, and thus the second connector 600b, can be secured in a plurality of locations relative to the first connector 600a which is coupled to the first support 181a.

Retractor blades 201 (designated herein as first and second retractor blades 201a, 201b) may be releasably secured to the arms 610 of the first and second connectors 600a, 600b of the surgical access system 5, as described above. While the retractor blades 201 shown coupled to the connectors 600 are tapered retractor blades, it should be understood that the retractor blades may be a straight, tapered, and/or angled retractor blades, such as those shown and described above, among other retractor blades within the purview of those skilled in the art.

Figure 19A:
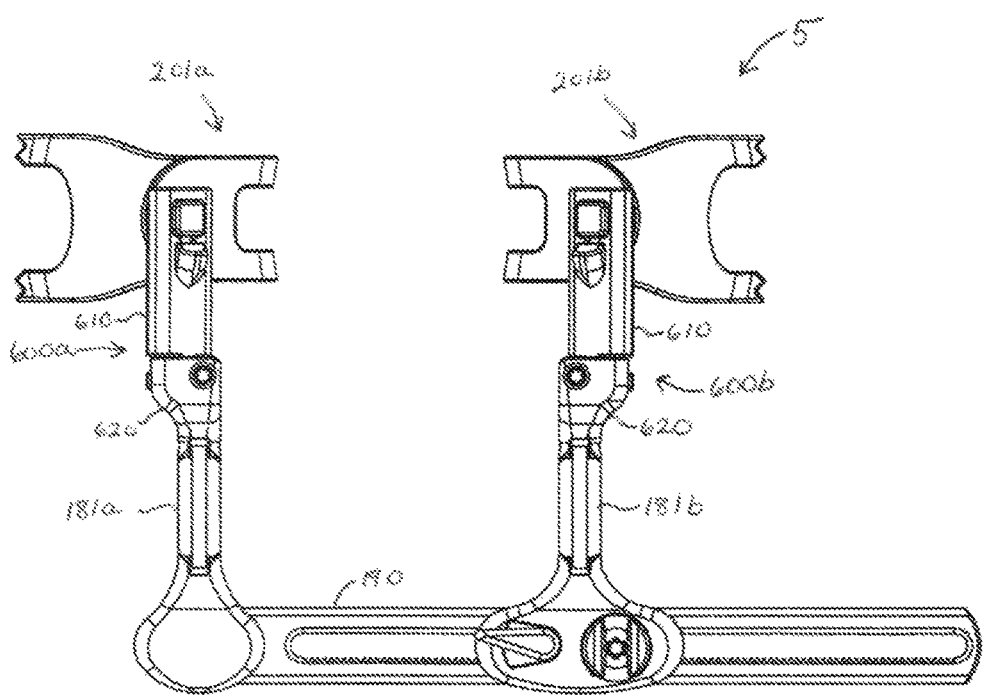
FIG. 19A is a top view of the surgical access system of FIGS. 18A and 18B, with the connectors in an angled position.
Figure 19B:
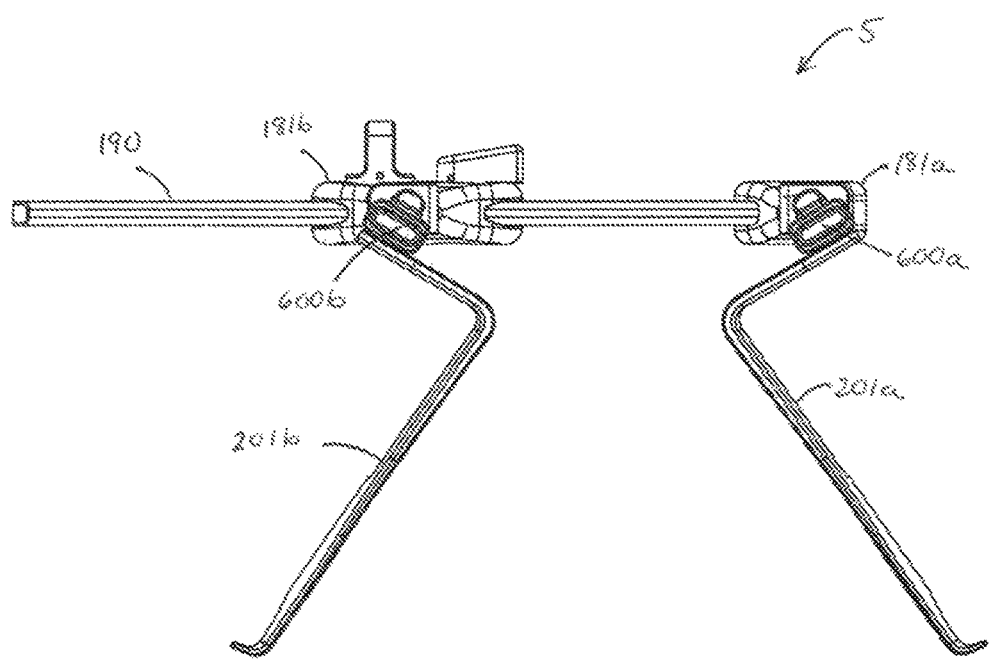
FIG. 19B is a side view of the surgical access system of FIG. 19A.

The arm 610 of the first and/or second connector 600a, 600b may be pivoted relative to its respective coupling element 620 by inserting a driving instrument (not shown)

into the recessed end 637 of the first gear 632 to rotate the first gear 632 which causes rotation of the second gear 634 (FIG. 17B) and thus, the arm 610 relative to the coupling element 620. The arms 610 may be rotated between a straight position shown in FIGS. 18A and 18B, and an angled position shown in FIGS. 19A and 19B, among a variety of other angles. The first gear 632 may be rotated in a first direction or a second direction to effect rotation of the arm 610 relative to the coupling element 620.

Figure 20C:
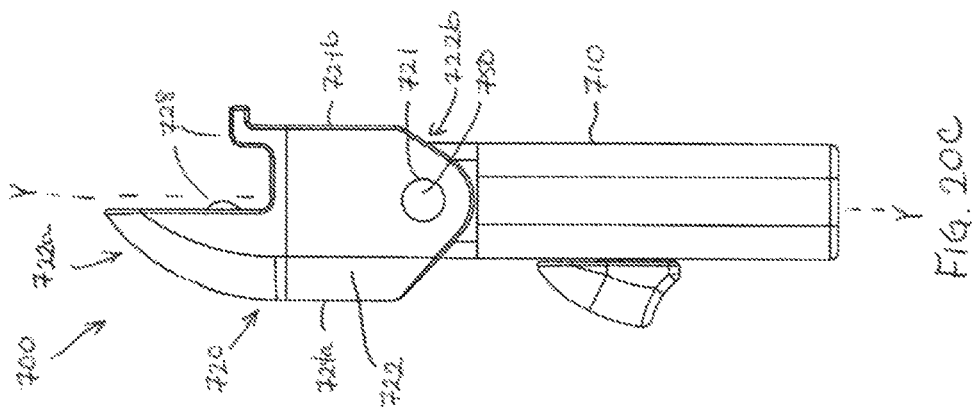
FIG. 20C is a side view of the connector of FIGS. 20A and 20B in a straight position.
Figure 20B:
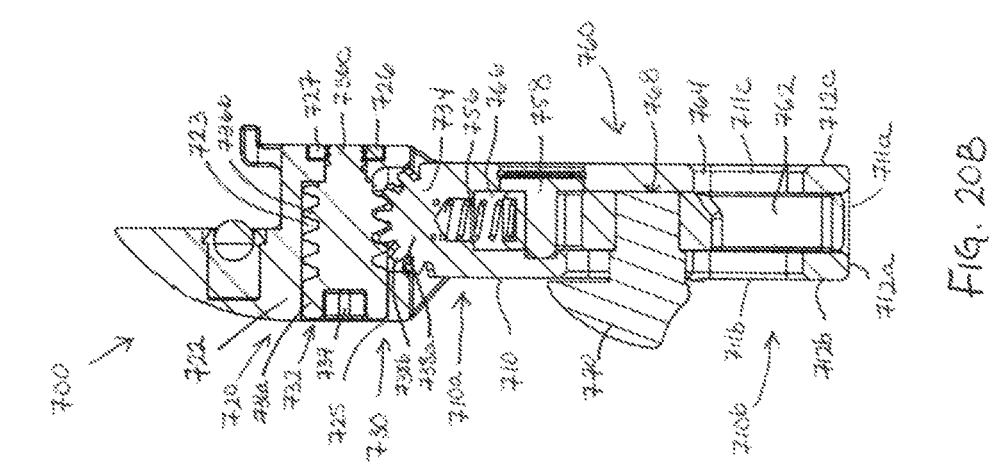
FIG. 20B is a cross-sectional view of the connector of FIG. 20A, taken along line 20B-20B of FIG. 20A.
Figure 20A:
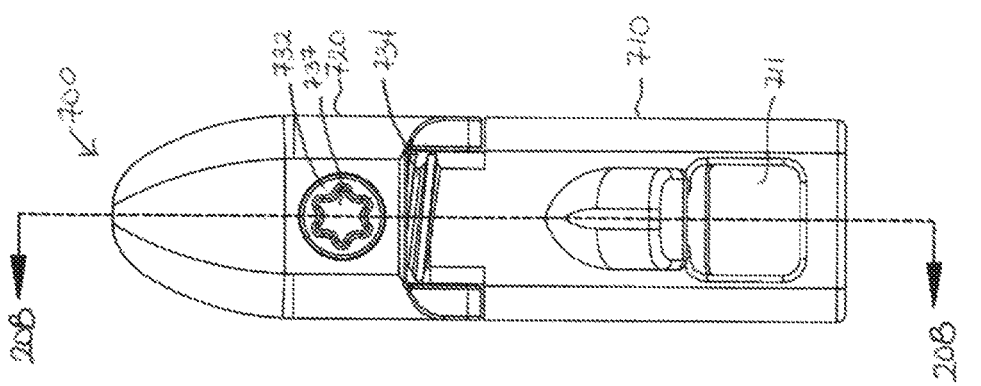
FIG. 20A is a top view of a connector in accordance with yet another embodiment of the present disclosure.

Referring now to FIGS. 20A-20C, a connector 700 in accordance with another embodiment of the present disclosure is shown. The connector 700 includes an arm 710, a coupling element 720, and a gear assembly 730 having a first gear 732 and a second gear 734. The arm 710 supports the second gear 734 and the coupling element 720 is configured and dimensioned to receive and support the first gear 732. The coupling element 720 is coupled to the arm 710 with the first and second gears 732, 734 meshingly engaged with each other such that rotation of the first gear 732 results in rotation of the second gear 734 which, in turn, pivots the arm 710 with respect to the coupling element 720.

The arm 710 includes a first end portion 710a and a second end portion 710b. The second gear 734 is non-rotatably secured to the first end portion 710a of the arm 710. In embodiments, the second gear 734 is integrally formed on the first end portion 710a of the arm 710. The second end portion 710b of the arm 710 includes a cavity 711 defined therein that is configured and dimensioned to house a receiving element 760 (FIG. 20B). The cavity 711 is open at a first opening 711a defined in a proximal surface 712a of the arm 710, a second opening 711b defined in a front surface 712b of the arm 710, and a third opening 711c defined in a back surface 712c of the arm 710.

The receiving element 760 is substantially similar to receiving element 160 and includes an engaging portion or first cavity 762 defined in a forked portion 764 of the receiving element 760, a second cavity 766 configured and dimensioned to engage a spring 756 and a stop 758, and a third cavity 768 disposed between the first and second cavities 762, 766 that is configured and dimensioned to receive a post 770. The engaging portion 762 engages the protruding portion 214 (see e.g., FIG. 23A) of the retractor blade 201 to releasably secure the retractor blade 201 to the arm 710, as described above with respect to receiving element 160.

The coupling element 720 includes a body section 722 having a cavity 723 defined therein that is configured and dimensioned to receive and support the first gear 732. First and second openings 725, 727 of the cavity 723 are defined in respective front and back surfaces 724a, 724b of the coupling element 720, and a nut 726 is coupled to the first gear 732 within the second opening 727 of the coupling element 720 to retain the first gear 732 within the cavity 723. The body section 722 includes a first end portion 722a including retaining features 728 for coupling with a cross bar 740 (see e.g., FIG. 22A), and a second end portion 722b including opposed openings 721 defined therethrough that are configured to receive a fixation pin 750 for securing the coupling element 720 to the arm 710.

The first gear 732 is in the form of a screw and includes a head portion 736a having a recessed end 737 configured to mate with a driving instrument (not shown), an elongated threaded body portion 736b, and a tail portion 736c. The first gear 732 is disposed within the cavity 723 of the coupling element 720 such that the recessed end 737 of the head portion 736a is accessible through the first opening 725 of the coupling element 720, and the tail portion 736b is secured within the second opening 727 of the coupling element 720 via the nut 726 to allow the first gear 732 to be rotated while being retained within the cavity 723 of the coupling element 720. In embodiments, the first gear 732 is a worm screw.

The second gear 734 is in the form of a wheel and includes a rounded body portion 738a having a toothed outer surface 738b. The second gear 734 is non-rotatably coupled to the first end portion 710a of the arm 710 and, in embodiments, integrally formed therewith. The toothed outer surface 738b of the second gear 734 is meshingly engaged with the elongated threaded body portion 736b of the first gear 732. In embodiments, the second gear 734 is a worm wheel.

Figure 21B:
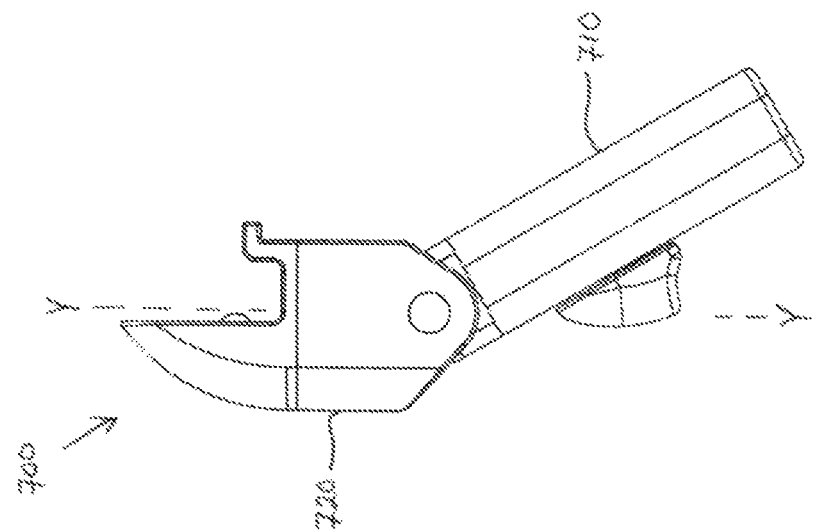
FIGS. 21A and 21B are side views of the connector of FIGS. 20A-20C in angled positions.
Figure 21A:
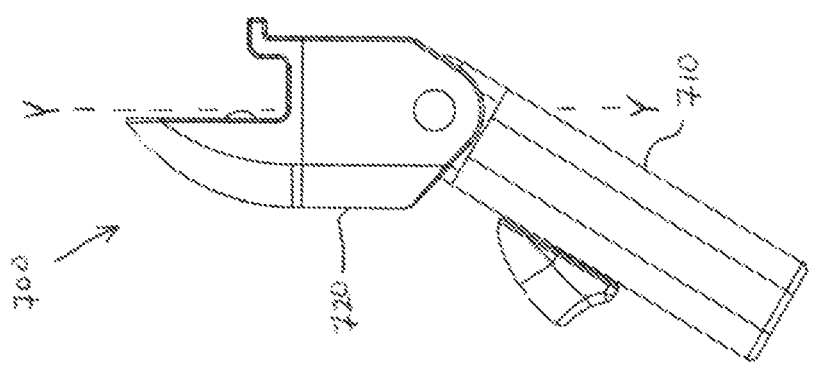

The arm 710 of the connector 700 is movable relative to the coupling element 720 from the straight position shown in FIGS. 20A-20C to angled positions shown, for example, in FIGS. 21A and 21B. The arm 710 of the connector 700 may be pivoted relative to the coupling element 720 about a longitudinal axis "Y" of the coupling element 720 by inserting a driving instrument (not shown) into the recessed end 737 (see e.g., FIG. 20B) of the first gear 732 to rotate the first gear 732 in a first or second direction which results in rotation of the second gear 734 and thus, the arm 710 relative to the coupling element 720. While two angled positions are shown in FIGS. 21A and 21B, it should be understood that the gear assembly 730 provides for fine adjustment of the arm 710 relative to the coupling element 720 about a range of angles.

Figure 22A:
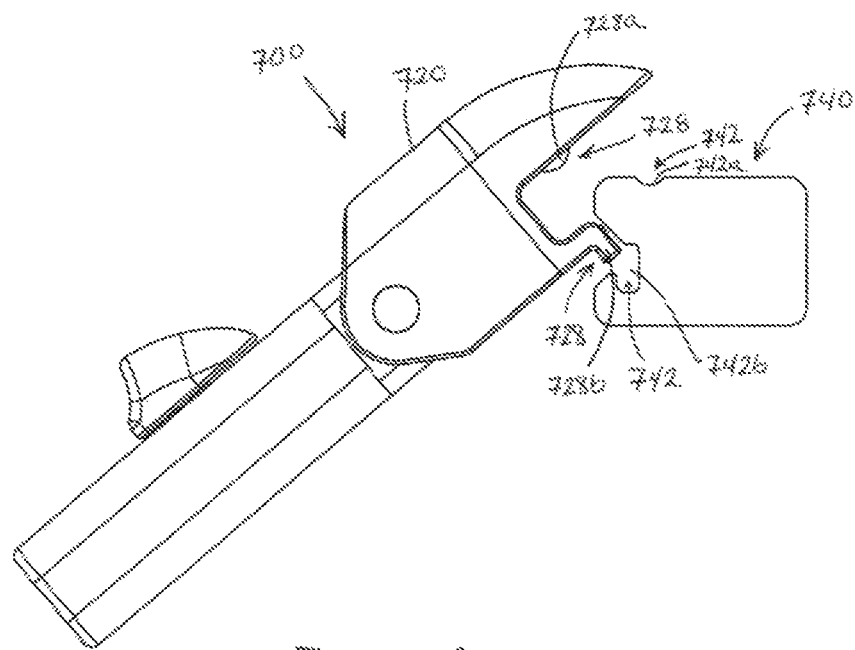
FIGS. 22A and 22B are side views of the connector of FIGS. 20A-20C and a cross bar.
Figure 22B:
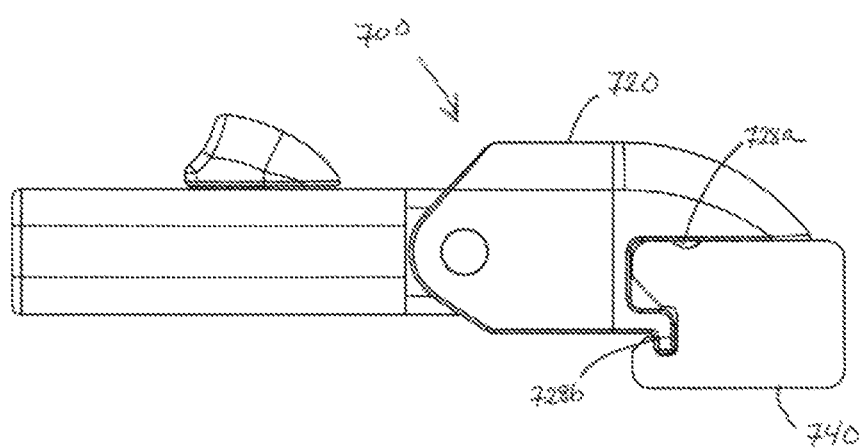

Turning now to FIGS. 22A and 22B, the connector 700 may be releasably coupled to a cross bar 740 via the retaining features 728 of the coupling element 720. The retaining features 728 of the coupling element 720 are configured to mate with retaining features 742 of the cross bar 740. In embodiments, the retaining features 728 of the coupling element include a protrusion 728a and a hook 728b configured to engage a recess 742a and a slot 742b of the retaining features 742 of the cross bar 740 to releasably secure the connector 700 to the cross bar 740.

Figure 23B:
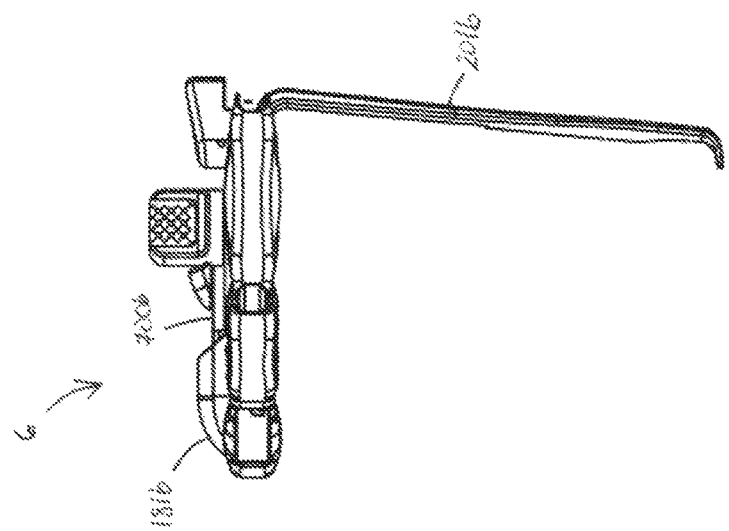
FIG. 23B is a side view of the surgical access system of FIG. 23A.
Figure 23A:
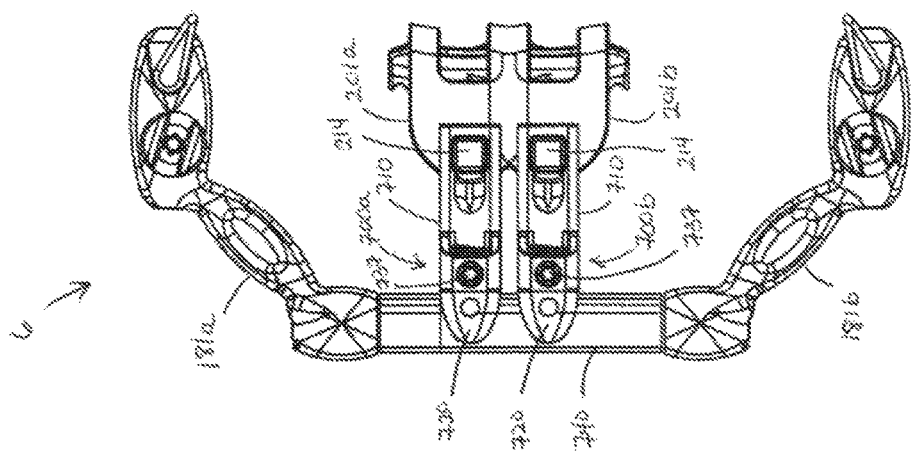
FIG. 23A is a top view of a surgical access system in accordance with another embodiment of the present disclosure, with connectors in a straight position.

The connector 700 and the cross bar 740 may be part of a surgical access system 6 as shown in FIGS. 23A and 23B. The surgical access system 6 includes a plurality of connectors 700 (designated first and second connectors 700a, 700b), a plurality of supports 181 (designated first and second supports 181a, 181b), and a cross bar 740 interconnecting the first and second supports 181a, 181b. The coupling elements 720 of the first and second connectors 700a, 700b are coupled to the cross bar 740 as shown, for example, in FIGS. 22A and 22B. The first and second supports 181a, 181b may further be coupled to respective beams 190 (see e.g., FIG. 18A), as described above.

Retractor blades 201 (designated herein as first and second retractor blades 201a, 201b) may be releasably secured to the arms 710 of the first and/or second connectors 700a, 700b of the surgical access system 6. While the retractor blades 201 shown coupled to the connectors 700 are tapered retractor blades, it should be understood that the retractor blades may be a straight, tapered, and/or angled retractor blades, such as those shown and described above, among other retractor blades within the purview of those skilled in the art.

Figure 24B:
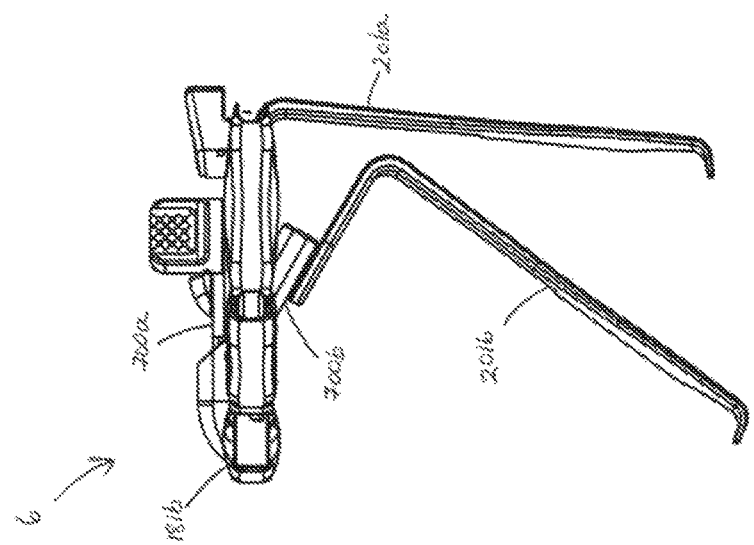
FIG. 24B is a side view of the surgical access system of FIG. 24A.
Figure 24A:
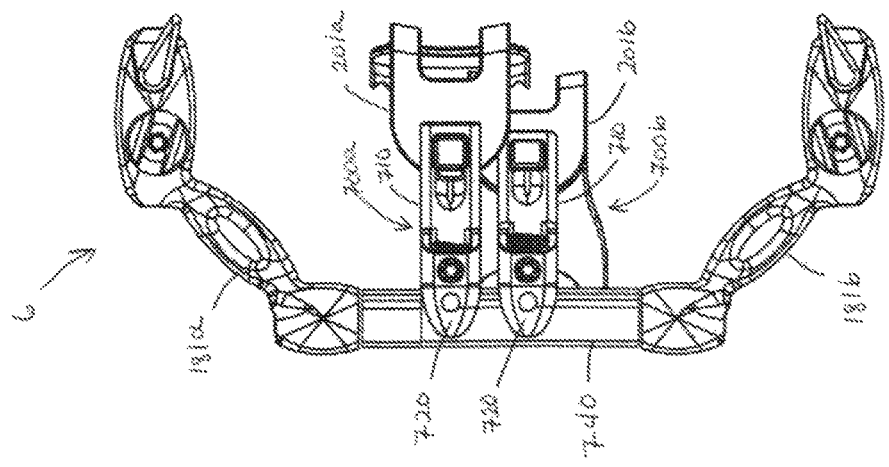
FIG. 24A is a top view of the surgical access system of FIGS. 23A and 23B, with one connector in an angled position.

The arm 710 of the first and/or second connectors 700a, 700b may be rotated relative to its respective coupling element 720 by inserting a driving instrument (not shown) into the recessed end 737 of the first gear 732 (see FIG. 20B) to rotate the first gear 732 which causes rotation of the second gear 734 and thus, the arm 710 relative to the coupling element 720. The arm(s) 710 may be rotated between a straight position shown in FIGS. 23A and 23B, and an angled position shown in FIGS. 24A and 24B, among a variety of other angles as described above.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A surgical access system comprising:
    a beam;
    a first support operably coupled to the beam; and
    a first connector operably connected to the first support, the first connector including:
        an arm including a first end portion and a second end portion, wherein the second end portion of the arm includes a cavity having a receiving element disposed therein, the receiving element including an engaging portion movable between a locked state and an unlocked state;
        a coupling element including a body portion defining a cavity therein; and
        a gear assembly including a first gear disposed within the cavity of the coupling element and a second gear non-rotatably disposed at the first end portion of the arm, the first and second gears meshingly engaged with each other such that rotation of the first gear results in rotation of the second gear which, in turn, causes the arm to pivot with respect to the coupling element; and
    a first retractor blade including a planar portion, the planar portion including a protruding portion releasably engaged with the engaging portion of the receiving element.

2. The surgical access system according to claim 1, wherein the first gear includes a head portion and an elongated threaded body portion terminating at a distal end.

3. The surgical access system according to claim 2, wherein an opening of the cavity is defined in a front surface of the coupling element, and the head portion of the first gear is accessible through the opening for rotating the first gear.

4. The surgical access system according to claim 2, wherein the first gear is a worm screw.

5. The surgical access system according to claim 1, wherein the second gear includes a rounded body portion having a toothed outer surface.

6. The surgical access system according to claim 5, wherein the second gear is a worm wheel.

7. The surgical access system according to claim 1, wherein the first retractor blade further includes
    a blade portion, the planar and blade portions extending along different planes.

8. The surgical access device according to claim 7, further including:
    a second support operably coupled to the beam;
    a second connector operably connected to the second support; and
    a second retractor blade releasably engaged to the second connector.

9. A surgical access system comprising:
    a first support;
    a second support;
    a cross bar interconnecting the first and second supports; and
    a first connector operably connected to the cross bar, the first connector including:
        an arm including a first end portion and a second end portion, wherein the second end portion of the arm includes a cavity having a receiving element disposed therein, the receiving element including an engaging portion movable along a receiving axis;
        a coupling element including a body portion defining a cavity therein; and
        a gear assembly including a first gear disposed within the cavity of the coupling element and a second gear non-rotatably disposed at the first end portion of the arm, the first and second gears meshingly engaged with each other such that rotation of the first gear results in rotation of the second gear which, in turn, causes the arm to pivot with respect to the coupling element about a pivot axis that is parallel to the receiving axis.

10. The surgical access system according to claim 9, wherein the first gear includes a head portion, an elongated threaded body portion, and a tail portion.

11. The surgical access system according to claim 10, wherein a first opening of the cavity is defined in a front surface of the coupling element, and the head portion of the first gear is accessible through the first opening for rotating the first gear.

12. The surgical access system according to claim 10, wherein the first gear is a worm screw.

13. The surgical access system according to claim 9, wherein the second gear includes a rounded body portion having a toothed outer surface.

14. The surgical access system according to claim 13, wherein the second gear is a worm wheel.

15. The surgical access system according to claim 9, wherein the second gear is integrally formed on the first end portion of the arm.

16. The surgical access system according to claim 9, wherein the engaging portion is movable between a locked state and an unlocked state.

17. The surgical access system according to claim 16, further including:
    a first retractor blade including:
        a planar portion including a protruding portion having a grooved defined therein, the protruding portion releasably engaged with the engaging portion of the receiving element; and
        a blade portion, the planar and blade portions extending along different planes.

18. The surgical access device according to claim 17, further including a second connector operably connected to the cross bar.

* * * * *